United States Patent
Ruggieri et al.

(12) 
(10) Patent No.: US 6,511,825 B1
(45) Date of Patent: Jan. 28, 2003

(54) CELL SIGNALING POLYPEPTIDES AND NUCLEIC ACIDS

(75) Inventors: Rosamaria Ruggieri, Nassau, NY (US); Marinella Callow, Richmond, CA (US); Paul W. Diaz, Irvine, CA (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/399,588

(22) Filed: Sep. 20, 1999

Related U.S. Application Data

(60) Provisional application No. 60/104,088, filed on Oct. 13, 1998.

(51) Int. Cl.[7] .................. C12P 21/06; A61K 38/00; C07K 2/00; C07K 4/00; C07K 5/00
(52) U.S. Cl. .................. 435/69.1; 530/300; 530/350; 536/1; 536/1.11; 536/18.7; 536/22.1; 536/23.1; 536/23.2; 536/23.5
(58) Field of Search ................ 536/1, 1.11, 18.7, 536/22.1, 23.1, 23.2, 23.5; 435/69.1; 530/300, 350

(56) References Cited

U.S. PATENT DOCUMENTS 5,817,479 A * 10/1998 Au-Young et al.

OTHER PUBLICATIONS

Nucleic acid database, Accession #AR044135, Sep. 29, 1999.*
Nucleic acid database, Accession #V33541, Dec. 29, 1998.*
Dudek et al, "Regulation of Neuronal Survival by the Serine–Threonine . . . " Science, (1997), V. 275, p. 661–665.
Emest24 Database Entry Hs1150670, Accession No. AA232750, Mar. 6, 1997, Hillier et al. WahU–Merck EST Project 1997.

* cited by examiner

Primary Examiner—Anthony C. Caputa
Assistant Examiner—Alana M. Harris
(74) Attorney, Agent, or Firm—Gregory Giotta

(57) ABSTRACT

The present invention relates to an isolated SRK polypeptide, biologically-active polypeptide fragments thereof, and nucleic acids which code for it. This polypeptide has various activities in regulating cell signaling and signal transduction pathways, including, e.g., a protein kinase activity; an autophosphorylating activity; a cell survival promoting activity; a HAX-1 binding activity; an apoptosis suppression activity; a MAPKK stimulatory activity; a transcription modulatory activity, and a SRK-specific immunogenic activity. The invention relates to all aspects of SRK, or homologs thereof, including assays for modulators, activators, ligands, etc. The invention also relates to a cytolic or soluble HAX-1 which produces apoptosis when expressed in cells.

11 Claims, 7 Drawing Sheets

```
  1 GCCCGCCCGGGAGCCAGATTTTGTGGAAGTATAATACTTTGTCATTATGAGATGTCGTCTCTCGGTGCCTCCTTTGTGCAAATTAAATTTGATGACTTGC
                                                              M  S  S  L  G  A  S  F  V  Q  I  K  F  D  D  L
101 AGTTTTTTGAAAACTGCGGTGGAGGAAGTTTTGGGAGTGTTTATCGAGCCAAATGGATATCACAGGACAAGGAGGTGGCTGTAAAGAAGCTCCTCAAAAT
     Q  F  F  E  N  C  G  G  G  S  F  G  S  V  Y  R  A  K  W  I  S  Q  D  K  E  V  A  V  K  K  L  L  K  I
201 AGAGAAAGAGGCAGAAATACTCAGTGTCCTCAGTCACAGAAACATCATCCAGTTTTATGGAGTAATTCTTGAACCTCCCAACTATGGCATTGTCACAGAA
     E  K  E  A  E  I  L  S  V  L  S  H  R  N  I  I  Q  F  Y  G  V  I  L  E  P  P  N  Y  G  I  V  T  E
301 TATGCTTCTCTGGGATCACTCTATGATTACATTAACAGTAACAGAAGTGAGGAGATGGATATGGATCACATTATGACCTGGGCCACTGATGTAGCCAAAG
     Y  A  S  L  G  S  L  Y  D  Y  I  N  S  N  R  S  E  E  M  D  M  D  H  I  M  T  W  A  T  D  V  A  K
401 GAATGCATTATTTACATATGGAGGCTCCTGTCAAGGTGATTCACAGAGACCTCAAGTCAAGAAACGTTGTTATAGCTGCTGATGGAGTATTGAAGATCTG
     G  M  H  Y  L  H  M  E  A  P  V  K  V  I  H  R  D  L  K  S  R  N  V  V  I  A  A  D  G  V  L  K  I  C
501 TGACTTTGGTGCCTCTCGGTTCCATAACCATACAACACACATGTCCTTGGTTGGAACTTTCCCATGGATGGCTCCAGAAGTTATCCAGAGTCTCCCTGTG
     D  F  G  A  S  R  F  H  N  H  T  T  H  M  S  L  V  G  T  F  P  W  M  A  P  E  V  I  Q  S  L  P  V
601 TCAGAAACTTGTGACACATATTCCTATGGTGTGGTTCTCTGGGAGATGCTAACAAGGGAGGTCCCCTTTAAAGGTTTGGAAGGATTACAAGTAGCTTGGC
     S  E  T  C  D  T  Y  S  Y  G  V  V  L  W  E  M  L  T  R  E  V  P  F  K  G  L  E  G  L  Q  V  A  W
701 TTGTAGTGGAAAAAAACGAGAGATTAACCATTCCAAGCAGTTGCCCCAGAAGTTTTGCTGAACTGTTACATCAGTGTTGGGAAGCTGATGCCAAGAAACG
     L  V  V  E  K  N  E  R  L  T  I  P  S  S  C  P  R  S  F  A  E  L  L  H  Q  C  W  E  A  D  A  K  K  R
801 GCCATCATTCAAGCAAATCATTTCAATCCTGGAGTCCATGTCAAATGACACGAGCCTTCCTGACAAGTGTAACTCATTCCTACACAACAAGGCGGAGTGG
     P  S  F  K  Q  I  I  S  I  L  E  S  M  S  N  D  T  S  L  P  D  K  C  N  S  F  L  H  N  K  A  E  W
901 AGGTGCGAAATTGAGGCAACTCTTGAGAGGCTAAAGAAACTAGAGCGTGATCTCAGCTTTAAGGAGCAGGAGCTTAAAGAACGAGAAAGACGTTTAAAGA
     R  C  E  I  E  A  T  L  E  R  L  K  K  L  E  R  D  L  S  F  K  E  Q  E  L  K  E  R  E  R  R  L  K
1001 TGTGGGAGCAAAAGCTGACAGAGCAGTCCAACACCCCGCTTCTCTTGCCTCTTGCTGCAAGAATGTCTGAGGAGTCTTACTTTGAATCTAAAACAGAGGA
      M  W  E  Q  K  L  T  E  Q  S  N  T  P  L  L  L  P  L  A  A  R  M  S  E  E  S  Y  F  E  S  K  T  E  E
1101 GTCAAACAGTGCAGAGATGTCATGTCAGATCACAGCAACAAGTAACGGGGAGGGCCATGGCATGAACCCAAGTCTGCAGGCCATGATGCTGATGGGCTTT
      S  N  S  A  E  M  S  C  Q  I  T  A  T  S  N  G  E  G  H  G  M  N  P  S  L  Q  A  M  M  L  M  G  F
1201 GGGGATATCTTCTCAATGAACAAAGCAGGAGCTGTGATGCATTCGGGATGCAGATAAACATGCAAGCCAAGCAGAATTCTTCCAAAACCACATCTAAGA
      G  D  I  F  S  M  N  K  A  G  A  V  M  H  S  G  M  Q  I  N  M  Q  A  K  Q  N  S  S  K  T  T  S  K
1301 GAAGGGGGAAGAAAGTCAACATGGCTCTGGGGTTCAGTGATTTTGACTTGTCAGAAGGTGACGATGATGATGATGACGGTGAGGAGGAGGATAATGA
      R  R  G  K  K  V  N  M  A  L  G  F  S  D  F  D  L  S  E  G  D  D  D  D  D  D  G  E  E  E  D  N  D
1401 CATGGATAATAGTGAATGAAAGCAGAAAGCAAAGTAATAAAATCACAAATGTTTGGAAAACACAAAAGTAACTTGTTTATCTCAGTCTGTACAAAAACAG
      M  D  N  S  E  *
1501 TAAGGAGGCAGAAAGCCAAGCACTGCATTTTTAGGCCAATCACATTTACATGACCGTAATTTCTTATCAATTCTACTTTTATTTTTGCTTACAGAAAAAC
1601 GGGGGGAGAATTAAGCCAAAGAAGTATATTTATGAATCAGCAAATGTGGTGCCTGATTATAGAAATTTGTGATCCCTATATACAATATAGGATTTTTAAA
1701 GTTGAGACATTCTGGCTTTTTCTTTTAATGAATACTTTTTAGTTTGTATTGGACTTTATTTCCTTTATTCAAATCATTTTTAAAAACTAACATTTTGAAC
1701 GTTGAGACATTCTGGCTTTTTCTTTTAATGAATACTTTTTAGTTTGTATTGGACTTTATTTCCTTTATTCAAATCATTTTTAAAAACTAACATTTTGAAC
1801 AAACATTCTTAACTCCTAATTGTTCTTAGACACGTAGTAATTCTGTGACATACTTTTTTTTTCTTATAGCAATACACTGTAATATCAGAAATGGTTGGCC
1901 TGAGCAACCTAGTAAGACTTCGTCTCTACTAATAATTAAAAAACTAGCTGGCATGGTAGCACACACCTGTAGTCCCAGATACTTGGGAGGCCAAGGCAGG
2001 AGGATTGCTTGAGACCTAGCAATCAGTCAGGGCTGCAGTGAGCCATGATGGCACCACTGCACTCTAGCCTGGGCAAGAGAACAAGATCCTGTCTCAAAAA
2101 ACAAAAAAAAAAAAAAAAAA
```

FIGURE 2

A
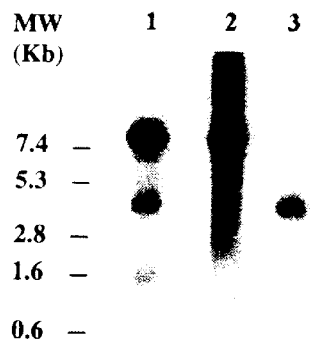
B
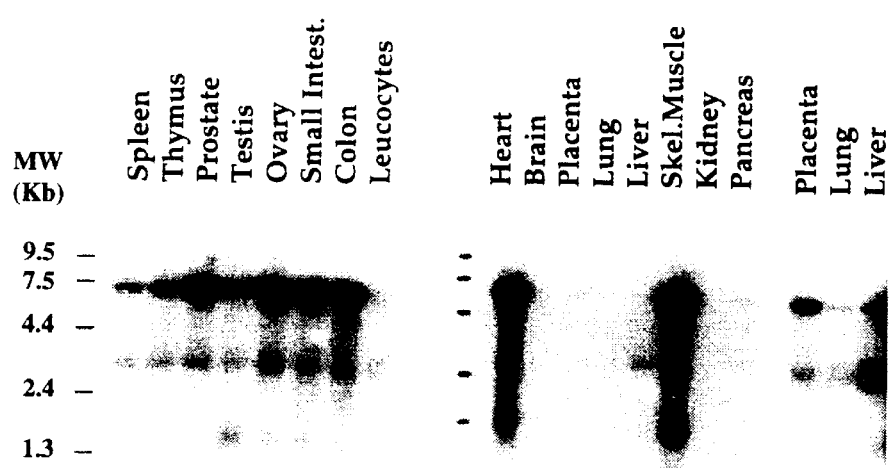
FIGURE 3

```
                                              M  S  L  F  D  L  F    7
TCCGGGGCTTTTTCGGCTTTCCTGGACCTCGGAGCCACAGAGATCCCTTTTTTGGAGGGA       240
    R  G  F  P  G  F  P  G  P  R  S  H  R  D  P  F  F  G  G  M    27
GGACTCGAGATGAAGATGATGATGAGGAAGAAGAAGAAGAAGGGGGCTCATGGGCCGTG        300
    T  R  D  E  D  D  D  E  E  E  E  E  E  G  G  S  W  G  R  G    47
GGAACCCAAGGTTCCATAGTCCTCAGCACCCCCCTGAGGAATTTGGCTTCGGCTTCAGCT       360
    N  P  R  F  H  S  P  Q  H  P  P  E  F  G  F  G  F  S  F       67
TCAGCCCAGGAGGAGGGATACGTTTCCACGATAACTTCGGCTTTGATGACCTAGTACGAG      420
    S  P  G  G  I  R  F  H  D  N  F  G  F  D  D  L  V  R  D       87
ATTTCAATAGCATCTTCAGCGATATGGGGGCCTGGACCTTGCCTTCCCATCCTCCTGAAC      480
    F  N  S  I  F  S  D  M  G  A  W  T  L  P  S  H  P  P  E  L    107
TTCCAGGTCCTGAGTCAGAGACACCTGGTGAGAGACTACGGGAGGGACAGACACTTCGGG      540
    P  G  P  E  S  E  T  P  G  E  R  L  R  E  G  Q  T  L  R  D    127
ACTCAATGCTTAAGTATCCAGATAGTCACCAGCCCAGGATCTTTGGGGGGTCTTGGAGA       600
    S  M  L  K  Y  P  D  S  H  Q  P  R  I  F  G  G  V  L  E  S    147
GTGATGCAAGAAGTGAATCCCCCCAACCAGCACCAGACTGGGGCTCCCAGAGGCCATTTC      660
    D  A  R  S  E  S  P  Q  P  A  P  D  W  G  S  Q  R  P  F       167
ATAGGTTTGATGATGTATGGCCTATGGACCCCCATCCTAGAACCAGAGAGGACAATGATC      720
    R  F  D  D  V  W  P  M  D  P  H  P  R  T  E  D  N  D  L       187
TTGATTCCCAGGTTTCCCAGGAGGGTCTTGGCCCCGGTTCTAACGCCCCAGCCCAAATCCT    780
    D  S  Q  V  S  Q  E  G  L  G  P  V  L  T  P  Q  P  K  S  Y    207
ATTTCAAGAGCATCTCTGTGACCAAGATCACTAAACCAGATGGGATAGTGGAGGAGCGCC     840
    F  K  S  I  S  V  T  K  I  T  K  P  D  G  I  V  E  E  R  R    227
GGACTGTGGTGGACAGTGAGGGCCGGACAGAGACTACAGTAACCCGACACGAAGCAGATA     900
    T  V  V  D  S  E  G  R  T  E  T  T  V  T  R  H  E  A  D  S    247
GCAGTCCTAGGGGTGATCCAGAATCACCAAGACCTCCAGCCCTGGATGATGCCTTTTCCA     960
    S  P  R  G  D  P  E  S  P  R  P  P  A  L  D  D  A  F  S  I    267
TCCTGGACTTATTCCTGGGACGTTGGTTCCGGTCCCGGTAGCCTTGTTAACCCTCAGAGG    1020
    L  D  L  F  L  G  R  W  F  R  S  R  *                         279
```

Figure 7

CELL SIGNALING POLYPEPTIDES AND NUCLEIC ACIDS

This Application claims priority from U.S. Provisional Application No. 60/104,088, filed Oct. 13, 1998.

BACKGROUND OF THE INVENTION

Mitogen-activated protein kinase (MAPK) pathways mediate a variety of signals that regulate cell growth and differentiation as well as stress-induced responses in organisms ranging from yeast to mammals (Lewis et al., *Adv Cancer Res*, 74:49–139, 1998). The pathways consist of a cascade of kinases, a serine/threonine kinase, MAPKKK, that phosphorylates and activates a dual specificity kinase, MAPKK that in turn is capable of transferring phosphates on to threonines and tyrosines of a third enzyme, MAPK. MAPK subsequently phosphorylates and activates transcription factors, among other substrates. In mammals, the prototype MAP kinase cascade is initiated by Ras (Howe et al., *Cell*, 71:335–342, 1992.) and includes Raf, MEK and ERK (Lewis et al., *Adv Cancer Res*, 74:49–139, 1998). In *Saccharomyces cerevisiae*, the best characterized MAP kinase cascade is the one responding to mating pheromones. In this system, Ste11 is the MAPKKK that activates Ste7, the MEK counterpart, which in turn activates two functionally redundant MAPKs, Fus3 (Elion et al., *Cell*, 60:649–664, 1990) and KSS 1 (Courchesne et al., *Cell*, 58:1107–1119, 1989). We and others (Freed et al., *Science*, 265:1713–1716, 1994; Irie et al., *Adv Cancer Res*., 265:1716–1719, 1994) have previously shown that loss of Ste11 by gene knock out in this system, can be functionally complemented by an active mammalian Raf protein and its substrate MEK. This hybrid MAP kinase pathway is uncoupled from mating pheromone stimulation and responds to Raf or MEK activators with expression of the HIS3 gene that allows growth on media lacking histidine.

BRIEF DESCRIPTION OF THE DRAWINGS

FIG. 2 shows a nucleotide and amino sequence coding for a human SRK.

FIG. 3A and FIG. 3B show Northern blot analysis using SRK cDNAs.

FIG. 7 shows an amino acid and nucleotide sequence of HAX-1.

DETAILED DESCRIPTION OF THE INVENTION

Figure 1:
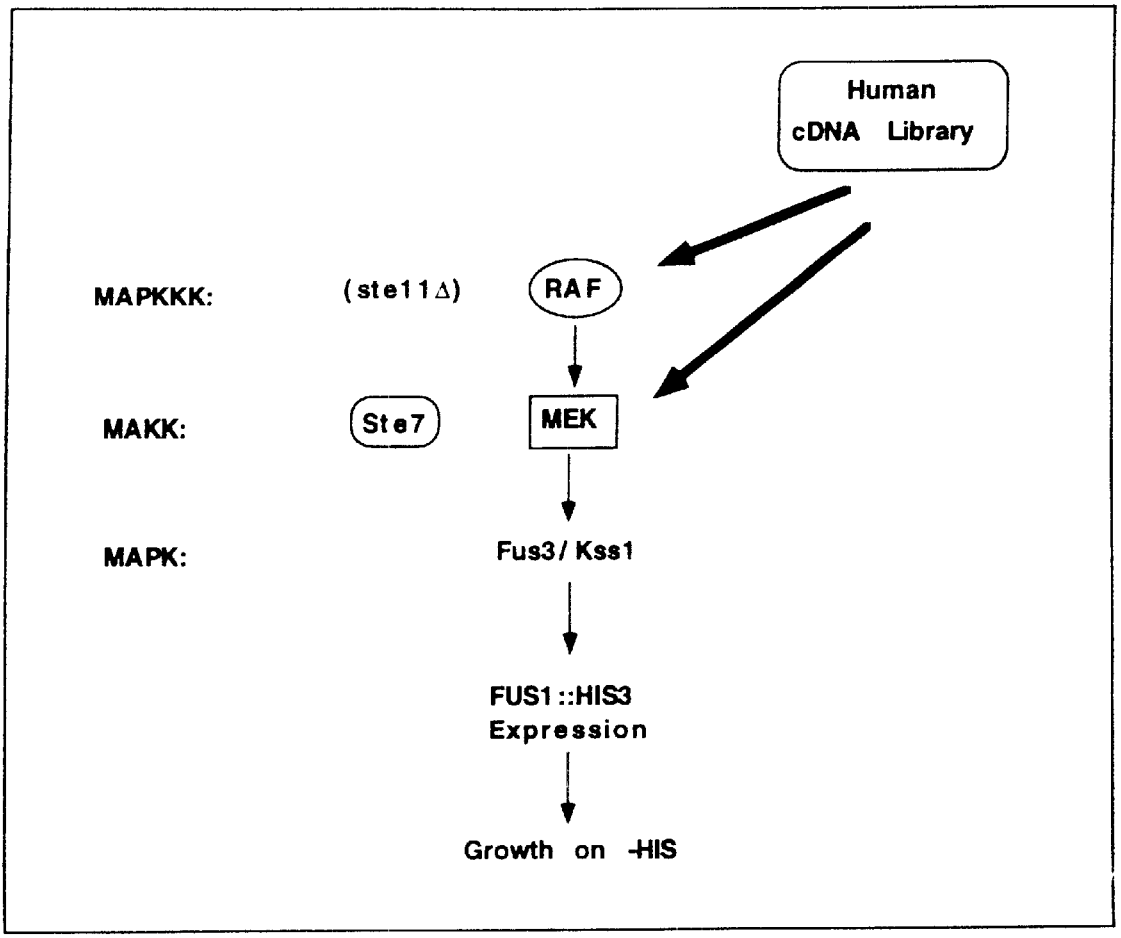
FIG. 1 is schematic drawing illustrating the strategy used to identify and clone SRK.

Novel nucleic acid and polypeptide sequences have been identified which code for a Survival Regulating Kinase (hereinafter, "SRK"), a class of proteins involved in cell signal transduction pathways, such as mitogen-activated protein kinase pathways. SRK, fragments thereof, and derivatives thereof, have one or more of the following biological activities, including, but not limited to: a protein kinase activity; an autophosphorylating activity; a cell growth-regulatory activity; a cell survival promoting activity; a HAX-1 binding activity; an apoptosis suppression activity; a MAPKK activation or stimulatory activity; a nuclear targeting activity; and a SRK-specific immunogenic activity.

A protein kinase activity means, e.g., that SRK, fragments, or derivatives thereof, can catalyze a reaction in which a phosphate group is transferred from a phosphate donor to a phosphate acceptor amino acid residue, preferably to a hydroxyl side chain of a serine or threonine. Substrates for SRK protein kinase activity, include, e.g., itself, MBP, and BAD. The protein kinase activity of SRK is similar to the activity of a MAPKKK, such as Raf (Bonner et al., *Nucleic Acid Res*., 14(2):1009–1015, 1986), Muk (Hirai et al., *Oncogene*, 12:641–650, 1996), TAK1 (Irie, *Science*, 165:1716–1719, 1994), and MLK (Dorow, *Eur J Biochem*, 213:701–710, 1993). Protein kinase activity can be identified routinely, e.g., as disclosed in Bagrodia et al., *J. Biol. Chem*., 270:27995–27998, 1995; Coso et al., *Cell*, 81:1137–1146, 1995; and in the examples below. By the term "autophosphorylating," it is meant that SRK can act as both the catalyst and the substrate in the protein kinase reaction.

SRK also possesses a binding activity to the HAX-1 (HS1-associated protein X-1) class of proteins. This activity can be measured in any suitable manner. For instance an in vivo assay using yeast two-hybrid screen can be utilized to detect binding activity between SRK and HAX-1. See, e.g., Braselmann and McCormick, *EMBO J*., 14:48394848, 1995; Chien et al., *Proc. Natl. Acad. Sci*., 88:9578–9582, 1991; and Fields and Song, *Nature*, 340:245–246, 1989. Binding activity can also be detected in vitro. SRK, fragments, or derivatives thereof, can be combined with a HAX-1 peptide (full-length HAX-1, or biologically-active fragments thereof) under conditions effective for binding to occur. Either the SRK or HAX peptides can be detectably labeled. The assay can be accomplished in liquid phase, where bound and free ligands are separated on beads, or, an assay can be accomplished in solid phase, as desired. Solid-phase assays can be performed using immunofluorescence, etc.

Another function possessed by SRK is an apoptosis suppression activity. Apoptosis is a programmed cell death in which cells undergo a characteristic morphological change where the cell and its nucleus shrink, condense, and frequently fragment. SRK, fragments, and derivatives, thereof, can suppress apoptosis. By "suppression," it is meant that SRK reduces, decreases, lessens, blocks, inhibits, etc., the number of the cells in the given population which would have undergone apoptosis in its absence. Thus, SRK has a cell survival promoting activity, as well.

The apoptosis suppression activity can be measured in various cell-based assays, e.g., by administering an SRK polypeptide (or derivative thereof) to cells under conditions in which a cell would normally undergo apoptosis, and observing the phenotypic effect of the polypeptide on apoptosis. Observable phenotypes of apoptosis, include, e.g., DNA fragmentation, clumps of condensed chromatin, disintegrating nuclear envelope, cell and nuclear shrinkage, etc. Any cell type programmed to undergo apoptosis can be used, e.g., Il-3 dependent cells, such as FL5.12 cells (e.g., withdrawal of IL-3 results in apoptosis), hemopoietic cells, fruit fly cells, and nematode cells. See, also below. The apoptosis suppression activity can also be measured in cells which have been engineered to undergo apoptosis, e.g., by the introduction of cell death genes, including, soluble Hax-1 (clone 104; see, examples), ced-9, etc. Thus, as described in the examples, introduction of a cell death gene into a cell elicits apoptosis; administration of an SRK polypeptide, or a derivative thereof, to the cell suppresses the phenotype.

A cell transforming activity can also be exhibited by SRK, fragments, and derivatives thereof. Such activity is displayed when SRK is expressed in the presence of an oncogenic ras, such as RasV12. This activity means, e.g., that when SRK is activated by an appropriate stimulus, a phenotypic change occurs in the host cell causing it to proliferate in an uncontrolled way, analogous to the defect observed in cancer cells. Transforming activity can be measured by any suitable method that assays for the loss of normal growth control, e.g., proliferation assays, focus formation assays, etc.

SRK can also activate MAPKK polypeptides, i.e., an MAPKK stimulatory activity. This activity can be direct, e.g., by directly acting upon the MAPKK (e.g., phosphorylating it), or it can be indirect where activation is accomplished by acting upon one or more intermediates which then stimulate MAPKK activity. An MAPKK stimulatory activity means, e.g., that SRK, and polypeptides thereof, activate or stimulate a MAPKK protein kinase activity. MAPKK stimulatory activity can be measured in vivo or in vitro as illustrated in the examples. MAPKK proteins stimulated or activated by SRK include, e.g., MEK and Ste7. In one type of assay, SRK is co-expressed in a cell with an MAPKK, the MAPKK is isolated, and then assayed for kinase activity using an appropriate substrate, e.g., ERK when MEK is used; Fus3 or KSS 1 when Ste7 is used. The amount of stimulatory activity can be determined by measuring the MAPKK kinase activity from cells transfected with and without SRK. MAPKK stimulatory activity can also be measured in cell-based assays. For instance, cell viability in cell lines defective in MAPKKK activity, such as cell lines lacking Raf or Ste11, are rescued when transformed with SRK. See, examples, below, for further guidance.

SRK is a member of a cell signal transduction pathway, one activity of which is to activate gene transcription. Expression analysis can be performed conventionally. For example, high-density oligonucleotide chip arrays can be designed to monitor expression. Such chips can contain all or subsets of the human genome. See, e.g., Anderson et al., Topics in *Current Chemistry*, Vol. 194, pages 117–129, 1998. Southern, *Current Biology*, 7:85–88, 1996; Marshall and Hodgson, *Nature Biotechnology*, 16:27–31, 1998.

By the term "SRK-specific immunogenic activity," it is meant that an SRK polypeptide elicits an immunological response which is selective for SRK. Such response can be cellular or humoral. Thus, the stimulation of antibodies, T-cells, macrophages, B-cells, dendritic cells, etc., by a SRK amino acid sequence selected from a mammalian SRK polypeptide, e.g., human as shown in FIG. 2, is a specific immunogenic activity. These responses can be measured routinely. See, for example, below where SRK-specific antibodies were generated against a C-terminus peptide.

A mammalian SRK, such as a human SRK, is a mammalian polypeptide having an amino acid sequence which is obtainable from a natural source and which has one or more of the mentioned activities. It can have a sequence as shown in FIG. 2, having an open-reading frame that begins with an initiation codon and ends with a stop codon. It can comprise a fragment of such sequence and possess a biological-activity as described above and below. It therefore includes naturally-occurring normal, mutant, polymorphic, etc., sequences. Natural sources include, e.g., living cells. e.g., obtained from tissues or whole organisms, cultured cell lines, including primary and immortalized cell lines, biopsied tissues, etc.

A human SRK, and related forms, of the present invention are coded for by at least three different RNA messages, about 7.5 Kb, 3.8 Kb, and 1.6 Kb. FIG. 2 shows an amino acid and nucleotide sequence of a SRK coded for by an mRNA of about 7.5 kb and cDNA clone of about 2 kb ("J42"). A cDNA coding for the 3.8 kb mRNA message was also identified. This cDNA is about 2.4 kb ("J207") and contains the same kinase domain as J42, but differs in its carboxy-terminus. The arrow in FIG. 2 indicates the end of sequences common to SRK and J207.

The present invention also relates to fragments of a mammalian SRK. The fragments are preferably "biologically active." By "biologically active," it is meant that the polypeptide fragment possesses an activity in a living system or with components of a living system. Biological activities include those mentioned, e.g., a protein kinase activity; an autophosphorylating activity; a cell growth-regulatory activity; a HAX-1 binding activity; an apoptosis suppression activity; a MAPKK activation activity; and a SRK-specific immunogenic activity. Fragments can be prepared according to any desired method, including, chemical synthesis, genetic engineering, cleavage products, etc. See, below. A biological-fragment of SRK includes a SRK which has had amino acid sequences removed or modified at either the carboxy- or amino-terminus of the protein, e.g., processing to a "mature" SRK from its pro-form.

The present invention also relates to a human SRK having a deduced sequence of amino acids 1 to 455 amino acids as shown in FIG. 2. The 455 amino acid polypeptide has a molecular weight of about 51 kilodaltons. It comprises the following domains: a kinase domain at about amino acids 23–250 (as discussed below, mutations within this region, e.g., at amino acids, 45, 46, and 133, affect kinase activity), a leucine zipper region at about amino acids 287–322, and an acidic domain at about amino acids 430–455.

A SRK polypeptide of the invention, e.g., having an amino acid sequence as shown in FIG. 2, can be analyzed by available methods to identify other structural and/or functional domains in the polypeptide, including membrane spanning regions, hydrophobic regions. For example, a SRK polypeptide can be analyzed by methods disclosed in, e.g., Kyte and Doolittle, *J. Mol. Bio.*, 157:105, 1982; EMBL Protein Predict; Rost and Sander, *Proteins*, 19:55–72, 1994.

Other SRK homologs from mammalian and non-mammalian sources can be obtained according to various methods. For example, hybridization with an oligonucleotide selected from the nucleotide sequence of a human SRK can be employed to select homologs from other species, e.g., as described in Sambrook et al., *Molecular Cloning*, Chapter 11, 1989. Such homologs can have varying amounts of nucleotide and amino acid sequence identity and similarity to SRK. Mammalian organisms include, e.g., rodents, mouse, rats, hamsters, monkeys, pigs, cows, etc. Non-mammalian organisms include, e.g., vertebrates, invertebrates, zebra fish, chicken, Drosophila, *C. elegans*, Xenopus, yeast such as *S. pombe, S. cerevisiae*, roundworms, prokaryotes, plants, Arabidopsis, viruses, etc.

The invention also relates to SRK specific amino acid sequences, e.g., a defined amino acid sequence which is found in the particular human of FIG. 2, but not in other amino acid sequences from non-SRK polypeptides. Comparisons between related proteins can be used to select sequences specific for SRK. A specific amino acid sequence can be found routinely, e.g., by searching a gene/protein database using the BLAST set of computer programs. A SRK specific amino acid sequence can be useful to produce peptides as antigens to generate an immune response specific for it. Antibodies obtained by such immunization can be used as a specific probe for a mammalian SRK protein for diagnostic or research purposes. SRK specific amino acid sequences include, e.g., amino acids AKQNSSKTTSKRRG as set forth in FIG. 2.

As mentioned, polypeptides of the present invention can comprise various amino acid sequences for a SRK (e.g., having a start and stop codon as shown in FIG. 2), a mature amino acid sequence (i.e., where the SRK polypeptide is produced as a precursor which is processed into a mature polypeptide, analogously to the peptide processing that occurs to Ras (e.g., Gelb, *Science*, 275:1750–1751, 1997), or fragments thereof. Useful fragments include, e.g., fragments comprising, or consisting essentially of, any of the aforementioned domains and SRK specific amino acid sequences.

A fragment of a SRK polypeptide can be selected to have a specific biological activity, e.g., a protein kinase activity; an autophosphor, lating activity; a cell growth-regulatory activity; a HAX-1 binding activity; an apoptosis suppression activity; a MAPKK activation or stimulatory activity; a transcription modulatory activity; a SRK-specific immunogenic activity; etc. A useful fragment can be identified routinely by testing such fragments for a desired activity. Useful fragments include, e.g., the following fragments of FIG. 2, 1–250, 1–23, 23–250, 251–455, 1–286, 287–322, 1–322, 323–455, 1–429, 430–455, etc.

The measurement of these activities is described below and in the examples. These peptides can also be identified and prepared as described in EP 496 162. A useful fragment can comprise, or consist essentially of, e.g., about nine contiguous amino acids, preferably about 10, 15, 20, 30, 40, etc. contiguous amino acids of FIG. 2.

A polypeptide of the present invention can also have 100% or less amino acid sequence identity to the amino acid sequence set forth in FIG. 2. For the purposes of the following discussion: Sequence identity means that the same nucleotide or amino acid which is found in the sequence set forth in FIG. 2 is found at the corresponding position of the compared sequence(s). A polypeptide having less than 100% sequence identity to the amino acid sequence set forth in FIG. 2 can contain various substitutions from the naturally-occurring sequence, including homologous and non-homologous amino acid substitutions. See below for examples of homologous amino acid substitution. The sum of the identical and homologous residues divided by the total number of residues in the sequence over which the SRK polypeptide is compared is equal to the percent sequence similarity. For purposes of calculating sequence identity and similarity, the compared sequences can be aligned and calculated according to any desired method, algorithm, computer program, etc., including, e.g., FASTA, BLASTA. A polypeptide having less than 100% amino acid sequence identity to the amino acid sequence of FIG. 2 can have about 99%, 98%, 97%, 95%, 90%, 70%, or as low as about 53% sequence identity. A preferred amount of amino acid sequence identity is about 87% or more, e.g., about 88%, 89%. See, below for discussion of mutations or muteins.

The present invention also relates to SRK polypeptide muteins, i.e., any polypeptide which has an amino acid sequence which differs in amino acid sequence from an amino acid sequence obtainable from a natural source (a fragment of a mammalian SRK does not differ in amino acid sequence from a naturally-occurring SRK). Thus, SRK muteins comprise amino acid substitutions, insertions, and deletions, including non-naturally occurring amino acids.

Muteins to a SRK amino acid sequence of the invention can also be prepared based on homology searching from gene data banks, e.g., Genbank, EMBL. Sequence homology searching can be accomplished using various methods, including algorithms described in the BLAST family of computer programs, the Smith-Waterman algorithm, etc. A mutein(s) can be introduced into a sequence by identifying and aligning amino acids within a domain which are identical and/or homologous between polypeptides and then modifying an amino acid based on such alignment. For instance, SRK shares 33% identity with Raf kinase (Bonner et al., *Nucleic Acid Res.*, 14(2):1009–1015, 1986), 37% with Muk (Hirai et al., *Oncogene*, 12:641–650, 1996), 39% with TAK1 (Irie, *Science*, 265:1716–1719, 1994) and 44% with MLK proteins (Dorow, *Eur J Biochem*, 213:701–710, 1993). These alignments reveal amino acid positions which are both identical and different from each other, providing information on amino acid substitutions that would be expected to reduce, decrease, or, eliminate a biological activity of SRK. For instance, where alignment reveals identical amino acids conserved between two or more domains, elimination or substitution of the amino acid(s) would be expected to adversely affect its biological activity.

Amino acid substitution can be made by replacing one homologous amino acid for another. Homologous amino acids can be defined based on the size of the side chain and degree of polarization, including, small nonpolar: cysteine, proline, alanine, threonine; small polar: serine, glycine, aspartate, asparagine; large polar: glutamate, glutamine, lysine, arginine; intermediate polarity: tyrosine, histidine, tryptophan; large nonpolar: phenylalanine, methionine, leucine, isoleucine, valine. Homologous acids can also be grouped as follows: uncharged polar R groups, glycine, serine, threonine, cysteine, tyrosine, asparagine, glutamine; acidic amino acids (negatively charged), aspartic acid and glutamic acid; basic amino acids (positively charged), lysine, arginine, histidine. Homologous amino acids also include those described by Dayhoff in the Atlas of *Protein Sequence and Structure* 5, 1978, and by Argos in *EMBO J.*, 8, 779–785, 1989.

Muteins in accordance with the present invention include amino acid sequences where a residue in the SRK sequence is replaced by a homologous residue from a corresponding kinase domains of the aforementioned proteins. Thus, the present invention relates to a SRK nucleotide sequence of FIG. 2, wherein said nucleic acid codes for a polypeptide and one or more amino acid positions are substituted or deleted, or both, and the polypeptide coded for by the nucleic acid has a kinase activity. For instance, a SRK polypeptide mutein, and its corresponding nucleotide coding sequence, can have an amino acid sequence as set forth in FIG. 2, except where one or more positions are substituted by homologous amino acids, e.g., where there are 1, 5, 10, 15, or 20 substitutions. The invention also relates to mutein polypeptides and mutein nucleic acids coding for such polypeptides. How a modification affects the mentioned activities can be measured according to the methods described above, below, and as the skilled worker in the field would know.

As mentioned, amino acid substitutions can also be made based on analogy to related proteins, such as other MAP-KKK proteins, including Raf, Ste11, Muk, TAK1, MLK, etc. For instance, replacement of one or two consecutive lysines at positions 45 and 46 to alanine (SRK-K45 A or SRK-KA; SRK-K45 AK46 A or SRK-KKAA) results in a dominant negative allele or a dominant interfering gene which has defective kinase activity. Similarly, substitution of aspartic acid at amino acid position 133 to alanine (SRK-D133 A or SRK-DA) results in a dominant negative allele or dominant interfering gene having defective kinase activity. The use of such muteins is described below. Other mutations could be selected routinely by modifying or mutating SRK, and selecting for those mutations that affect one or more its activities, e.g., by measuring kinase activity according to the methods and examples described below.

A mammalian SRK polypeptide, fragment, or substituted polypeptide can also comprise various modifications, where such modifications include lipid modification, methylation, phosphorylation, glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

Polypeptides of the present invention (e.g., human SRK, fragments thereof, mutations thereof) can be used in various ways, e.g., in assays, as immunogens for antibodies as described below, as biologically-active agents (e.g., having one or more of the activities associated with SRK).

A polypeptide coding for a SRK, a derivative thereof, or a fragment thereof, can be combined with one or more structural domains, functional domains, detectable domains, antigenic domains, and/or a desired polypeptide of interest, in an arrangement which does not occur in nature, i.e., not naturally-occurring, e.g., as in a human or SRK gene, a genomic fragment prepared from the genome of a living organism, e.g., an animal, preferably a mammal, such as human, mouse, or cell lines thereof. A polypeptide comprising such features is a chimeric or fusion polypeptide. Such a chimeric polypeptide can be prepared according to various methods, including, chemical, synthetic, quasisynthetic, and/or recombinant methods. A chimeric nucleic acid coding for a chimeric polypeptide can contain the various domains or desired polypeptides in a continuous (e.g., with multiple N-terminal domains to stabilize or enhance activity) or interrupted open reading frame, e.g., containing introns, splice sites, enhancers, etc. The chimeric nucleic acid can be produced according to various methods. See, e.g., U.S. Pat. No. 5,439,819. A domain or desired polypeptide can possess any desired property, including, a biological function such as signaling, growth promoting, cellular targeting (e.g., signal sequence, targeting sequence, such as targeting to the endoplasmic reticulum or nucleus), etc., a structural function such as hydrophobic, hydrophilic, membrane-spanning, etc., receptor-ligand functions, and/or detectable functions, e.g., combined with enzyme, fluorescent polypeptide, green fluorescent protein, (Chalfie et al., *Science*, 263:802, 1994; Cheng et al., *Nature Biotechnology*, 14:606, 1996; Levy et al., *Nature Biotechnology*, 14:610, 1996, etc. In addition, a polypeptide, or a part of it, can be used as a selectable marker when introduced into a host cell. For example, a nucleic acid coding for an amino acid sequence according to the present invention can be fused in-frame to a desired coding sequence and act as a tag for purification, selection, or marking purposes. The region of fusion can encode a cleavage site to facilitate expression, isolation, purification, etc.

A polypeptide according to the present invention can be produced in an expression system, e.g., in vivo, in vitro, cell-free, recombinant, cell fusion, etc., according to the present invention. Modifications to the polypeptide imparted by such systems include glycosylation, amino acid substitution (e.g., by differing codon usage), polypeptide processing such as digestion, cleavage, endopeptidase or exopeptidase activity, attachment of chemical moieties, including lipids and phosphates, etc.

A polypeptide according to the present invention can be recovered from natural sources, transformed host cells (culture medium or cells) according to the usual methods, including, detergent extraction (e.g., CHAPS, octylglucoside), ammonium sulfate or ethanol precipitation, acid extraction, anion or cation exchange chromatography, phosphocellulose chromatography, hydrophobic interaction chromatography, hydroxyapatite chromatography and lectin chromatography. Protein refolding steps can be used, as necessary, in completing the configuration of the mature protein. Finally, high performance liquid chromatography (HPLC) can be employed for purification steps. A SRK polypeptide can also be isolated as described for other MAPKKK proteins as the skilled worker would know.

A mammalian SRK nucleic acid, or fragment thereof, is a nucleic acid having a nucleotide sequence obtainable from a natural source. See, above. It therefore includes naturally-occurring, normal, mutant, polymorphic alleles, etc. Natural sources include, e.g., living cells obtained from tissues and whole organisms, cultured cell lines, including primary and immortalized cell lines.

As already discussed, human SRK is expressed as multiple mRNA species. For example, Northern blot analysis using a cDNA probe from the kinase domain identified a predominant band of 7.5 Kb and less abundant forms of 3.8 Kb and 1.6 Kb. A specific probe from the 3' end of the J42 clone identified the large transcript as J42 mRNA, whereas a probe from the 3' end of the J207 clone recognized the 3.8 Kb message. Analysis of mRNA distribution indicated that J42 and J207 are ubiquitously expressed in normal tissues, but are most abundant in skeletal muscle and heart. These clones differ in the 3' end; e.g., J42 contains an acidic region which is lacking in J207. The region where the clones diverge in sequence is indicated in FIG. 2 by the arrow. Thus, probes derived from these regions (both nucleic acid and antibody) can be useful to distinguish between them, e.g., on blots, for differential display, in tissue sections, samples, etc.

A nucleic acid sequence of the invention can contain the complete coding sequence from amino acid 1 to amino acid 455, degenerate sequences thereof, and fragments thereof. A nucleic acid according to the present invention can also comprise a nucleotide sequence which is 100% complementary, e.g., an anti-sense, to any nucleotide sequence mentioned above and below.

A nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell or tissue (e.g., from an embryonic or adult heart or skeletal cells or tissues) at a particular stage of development, having a desired genotype, phenotype etc.

As described for SRK polypeptides mentioned above, a nucleic acid comprising a nucleotide sequence coding for a polypeptide according to the present invention can include only coding sequence; a coding sequence and additional coding sequence (e.g., sequences coding for leader, secretory, targeting, enzymatic, fluorescent or other diagnostic peptides), coding sequences and non-coding sequences, e.g., untranslated sequences at either a 5' or 3' end, or dispersed in the coding sequence, e.g., introns. A nucleic acid comprising a nucleotide sequence coding without interruption for a polypeptide means that the nucleotide sequence contains an amino acid coding sequence for a SRK, with no non-coding nucleotides interrupting or intervening in the coding sequence, e.g., absent intron(s). Such a nucleotide sequence can also be described as contiguous. A genomic DNA coding for a human or other mammalian SRK, etc., can be obtained routinely.

A nucleic acid according to the present invention also can comprise an expression control sequence operably linked to a nucleic acid as described above. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, tanscriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids, and their complements, which hybridize to a nucleic acid comprising a nucleotide sequence as set forth in FIG. 2. A nucleotide sequence hybridizing to the latter sequence will have a complementary nucleic acid strand, or act as a template for one in the presence of a polymerase (i.e., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in FIG. 2. A nucleic acid capable of hybridizing to such sequence, preferably, possesses, e.g., about 85%, more preferably, 90%, 92%, and even more preferably, 95%, 97%, or 100% complementarity, between the sequences. The present invention particularly relates to nucleic acid sequences which hybridize to the nucleotide sequence set forth in FIG. 2 under low or high stringency conditions.

Nucleic acids which hybridize to SRK sequences can be selected in various ways. For instance, blots (i.e., matrices containing nucleic acid), chip arrays, and other matrices comprising nucleic acids of interest, can be incubated in a prehybridization solution (6×SSC, 0.5% SDS, 100 μg/ml denatured salmon sperm DNA, 5×Denhardt's solution, and 50% formamide), at 30EC, overnight, and then hybridized with a detectably SRK probe (see below) in a hybridization solution (e.g., 6×SSC, 0.5% SDS, 100 μg/ml denatured salmon sperm DNA and 50% formamide), at 42EC, overnight in accordance with known procedures. Blots can be washed at high stringency conditions that allow, e.g., for less than 5% bp mismatch (e.g., wash twice in 0.1% SSC and 0.1% SDS for 30 min at 65EC), i.e., selecting sequences having 95% or greater sequence identity. Other non-limiting examples of high stringency conditions includes a final wash at 65EC in aqueous buffer containing 30 mM NaCl and 0.5% SDS. Another example of high stringent conditions is hybridization in 7% SDS, 0.5 M NaPO$_4$, pH 7, 1 mM EDTA at 50EC, e.g., overnight, followed by one or more washes with a 1% SDS solution at 42EC. The activated SRK and dominant negative SRK sequences described herein hybridize to the wild-type nucleic acid sequence in FIG. 2, and oligonucleotide probes thereof, under the aforementioned high stringency conditions. Whereas high stringency washes can allow for less than 5% mismatch, relaxed or low stringency wash conditions (e.g., wash twice in 0.2% SSC and 0.5% SDS for 30 min at 37EC) can permit up to 20% mismatch. Another non-limiting example of low stringency conditions includes a final wash at 42EC in a buffer containing 30 mM NaCl and 0.5% SDS. Washing and hybridization can also be performed as described in Sambrook et al., *Molecular Cloning*, 1989, Chapter 9.

Hybridization can also be based on a calculation of melting temperature (Tm) of the hybrid formed between the probe and its target, as described in Sambrook et al. Generally, the temperature $T_m$ at which a short oligonucleotide (containing 18 nucleotides or fewer) will melt from its target sequence is given by the following equation: $T_m$=(number of A's and T's)×2° C.+(number of C's and G's)×4° C. For longer molecules, $T_m$=81.5+16.6log$_{10}$[Na$^+$]+0.41 (%GC)−600/N where [Na$^+$] is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 95%, preferably 97%, nucleotide complementarity between the probe (e.g., an oligonucleotide of SRK) and target nucleic acid (a SRK mutein or homolog).

According to the present invention, a nucleic acid or polypeptide can comprise one or more differences in the nucleotide or amino acid sequence set forth in FIG. 2. Changes or modifications to the nucleotide and/or amino acid sequence can be accomplished by any method available, including directed or random mutagenesis.

A nucleic acid coding for a human SRK according to the invention can comprise nucleotides which occur in a naturally-occurring SRK gene e.g., naturally-occurring polymorphisms, normal or mutant alleles (nucleotide or amino acid), mutations which are discovered in a natural population of mammals, such as humans, monkeys, pigs, mice, rats, or rabbits. By the term naturally-occurring, it is meant that the nucleic acid is obtainable from a natural source, e.g., animal tissue and cells, body fluids, tissue culture cells, forensic samples. Naturally-occurring mutations can include deletions (e.g., a truncated amino- or carboxy-terminus), substitutions, inversions, or additions of nucleotide sequence. These genes can be detected and isolated by nucleic acid hybridization according to methods which one skilled in the art would know. A nucleotide sequence coding for a human SRK polypeptide of the invention can contain codons found in a naturally-occurring gene, transcript, or cDNA, for example, e.g., as set forth in FIG. 2, or it can contain degenerate codons coding for the same amino acid sequences. For instance, it may be desirable to change the codons in the sequence to optimize the sequence for expression in a desired host.

A nucleic acid according to the present invention can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAase H, improved in vivo stability, etc. See, e.g., U.S. Pat. No. 5,378,825.

Various modifications can be made to the nucleic acids, such as attaching detectable markers (avidin, biotin, radioactive elements), moieties which improve hybridization, detection, or stability. The nucleic acids can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967; 5,476,925; 5,478,893.

Another aspect of the present invention relates to oligonucleotides or nucleic acid probes. Such oligonucleotides or nucleic acid probes can be used, e.g., to detect, quantitate, or isolate a mammalian SRK nucleic acid in a test sample, or to identify SRK homologs. In a preferred embodiment, the nucleic acids can be utilized as oligonucleotide probes, e.g., in PCR, differential display, in combination with cDNA libraries, expression libraries, etc. Detection can be desirable for a variety of different purposes, including research, diagnostic, and forensic. For diagnostic purposes, it may be desirable to identify the presence or quantity of a nucleic acid sequence in a sample, where the sample is obtained from tissue, cells, body fluids, etc. In a preferred method, the present invention relates to a method of detecting a nucleic acid comprising, contacting a target nucleic acid in a test sample with an oligonucleotide under conditions effective to achieve hybridization between the target and oligonucleotide; and detecting hybridization. An oligonucleotide in accordance with the invention can also be used in synthetic nucleic acid amplification such as PCR (e.g., Saiki et al., *Science*, 241:53, 1988; U.S. Pat. No. 4,683,202; PCR Protocols: A *Guide to Methods and Applications*, Innis et al., eds., Academic Press, New York, 1990); differential display (See, e.g., Liang et al., *Nucl. Acid. Res.*, 21:3269–3275, 1993; U.S. Pat. No. 5,599,672; WO97/18454).

Detection can be accomplished in combination with oligonucleotides for other genes, e.g., genes involved in signal transduction, growth, cancer, apoptosis, or any of the genes mentioned above or below, etc. Oligonucleotides can also be used to test for mutations, e.g., using mismatch DNA repair technology as described in U.S. Pat. No. 5,683,877; U.S. Pat. No. 5,656,430; Wu et al., *Proc. Natl. Acad. Sci.*, 89:8779–8783, 1992.

Oligonucleotides of the present invention can comprise any continuous nucleotide sequence of FIG. 2 or a complement thereto. These oligonucleotides (nucleic acid) according to the present invention can be of any desired size, e.g., about 10–200 nucleotides, 12–100, preferably 12–50, 12–25, 14–16, at least about 15, at least about 20, etc. The oligonucleotides can have non-naturally-occurring nucleotides, e.g., inosine, AZT, 3TC, etc. The oligonucleotides can have 100% identity or complementarity to a sequence of FIG. 2, or it can have mismatches or nucleotide substitutions, e.g., 1, 2, 3, 4, or 5 substitutions. In accordance with the present invention, the oligonucleotide can comprise a kit, where the kit includes a desired buffer (e.g., phosphate, tris, etc.), detection compositions, etc. The oligonucleotide can be labeled or unlabeled, with radioactive or non-radioactive labels as known in the art.

Another aspect of the present invention is a nucleotide sequence which is unique to human SRK. By a unique sequence to a SRK, it is meant a defined order of nucleotides which occurs in SRK, e.g., in the nucleotide sequence of FIG. 2, but rarely or infrequently in other nucleic acids, especially not in an animal nucleic acid, preferably mammal, such as human, rat, mouse, etc. Unique nucleotide sequences include the sequences, or complements thereto, coding for amino acids AKQNSSKTTSKRRG. Such sequences can be used as probes in any of the methods described herein or incorporated by reference. Both sense and antisense nucleotide sequences are included. A unique nucleic acid according to the present invention can be determined routinely. A nucleic acid comprising such a unique sequence can be used as a hybridization probe to identify the presence of, e.g., human or mouse SRK, in a sample comprising a mixture of nucleic acids, e.g., on a Northern blot. Hybridization can be performed under high stringent conditions (see, above) to select nucleic acids (and their complements which can contain the coding sequence) having at least 95% identity (i.e., complementarity) to the probe, but less stringent conditions can also be used. A unique SRK nucleotide sequence can also be fused in-frame, at either its 5' or 3' end, to various nucleotide sequences as mentioned throughout the patent, including coding sequences for other parts of SRK, enzymes, GFP, etc, expression control sequences, etc.

As already discussed, hybridization can be performed under different conditions, depending on the desired selectivity, e.g., as described in Sambrook et al., *Molecular Cloning*, 1989. For example, to specifically detect human or mouse SRK, an oligonucleotide can be hybridized to a target nucleic acid under conditions in which the oligonucleotide only hybridizes to it, e.g., where the oligonucleotide is 100% complementary to the target. Different conditions can be used if it is desired to select target nucleic acids which have less than 100% nucleotide complementarity, at least about, e.g., 99%, 97%, 95%, 90%, 70%, 67%.

Anti-sense nucleic acid can also be prepared from a nucleic acid according to the present invention, preferably an anti-sense to a coding sequence of FIG. 2. Antisense nucleic acid can be used in various ways, such as to regulate or modulate expression of SRK, e.g., inhibit it, to detect its expression, or for in situ hybridization. These oligonucleotides can be used analogously to U.S. Pat. No. 5,576,208. For the purposes of regulating or modulating expression of SRK, an anti-sense oligonucleotide can be operably linked to an expression control sequence.

The nucleic acid according to the present invention can be labeled according to any desired method. The nucleic acid can be labeled using radioactive tracers such as $^{32}P$, $^{35}S$, $^{125}I$, $^3H$, or $^{14}C$, to mention some commonly used tracers. The radioactive labeling can be carried out according to any method such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

A nucleic acid according to the present invention, including oligonucleotides, antisense nucleic acid, etc., can be used to detect expression of SRK in whole organs, tissues, cells, etc., by various techniques, including Northern blot, PCR, in situ hybridization, etc. Such nucleic acids can be particularly useful to detect disturbed expression, e.g., cell-specific and/or subcellular alterations, of SRK. The levels of SRK can be determined alone or in combination with other gene products, especially cardiac, skeletal, and cell death specific gene products, or other gene products involved in cell signaling and regulation. A nucleic acid according to the present invention can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. A nucleic acid can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a nucleic acid of the present invention has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells (e.g., COS, CV1, BHK, CHO, HeLa, LTK, NIH 3T3, 293, PAE, human, human fibroblast, human primary tumor cells, testes cells), insect cells, such as Sf9 (S. frugipeda) and Drosophila, bacteria, such as E. coli, Streptococcus, bacillus, yeast, such as Sacharomyces, S. cerevisiae (e.g., cdc mutants, cdc25, cell cycle and division mutants, such as ATCC Nos. 42563, 46572, 46573, 44822, 44823, 46590, 46605, 42414, 44824, 42029, 44825, 44826, 42413, 200626, 28199, 200238, 74155, 44827, 74154, 74099, 201204, 48894, 42564, 201487, 48893, 28199, 38598, 201391, 201392), YRG2, fungal cells, plant cells, embryonic stem cells (e.g., mammalian, such as mouse or human), fibroblasts, muscle cells, cardiac cells, T-cells (helper, CD4, CD8), B-cells, macrophages, hemopoietic cells, lymphocytes, Th1, Th2, etc.

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, promoters of other genes in the cell signal transduction pathway, MMTV, SV40, trp, lac, tac, or T7 promoters for bacterial hosts; or alpha factor, alcohol oxidase, or PGH promoters for yeast.

Another gene of interest can be introduced into the same host for purposes of, e.g., modulating SRK function. Such genes can be the normal gene, or a variation, e.g., a mutation, chimera, polymorphism, etc. Such genes include, e.g., members of the same or related signaling pathways, e.g., Ras family, RasV12, Cdc42Hs, Racs, Rhos, PAKS, JNK, Jun, WASP, IQGAP, POSH, POR1, p67-phox, MLK3, MAP kinases, NCK, SOS, ERKs, p38, GEFs, GAPs, GDIs, Wiskott-Aldrich Syndrome protein, FTases, STE14, p53, Rb, Mtase, GTPases subunits, Dbl, lbc, Ost, Lsc, STATS, Raf, src, Jun, fos, elk, MEK, Ste11, Ste7, etc.

A nucleic acid or polypeptide of the present invention can be used as a size marker in nucleic acid or protein electrophoresis, chromatography, etc. Defined restriction fragments can be determined by scanning the sequence for restriction sites, calculating the size, and performing the corresponding restriction digest. A SRK cDNA as shown in FIG. 2 can be used as a molecular weight marker in nucleic acid electrophoresis.

Another aspect of the present invention relates to the regulation of biological pathways in which a SRK gene is involved, particularly programmed cell death (e.g., as involved in the maintenance and survival of various cell types, including immune, skeletal, and cardiac cells), cell signaling, signal transduction, ligand-activated responses, pathological conditions, such as cancer, cardiopulmonary disease, autoimmune disease (multiple sclerosis, lupus, rheumatoid arthritis, etc. For instance, it has been observed that tolerance can be mediated by deletion or apoptosis of suppressor T cells. See, e.g., Chen et al., Nature, 376: 177–180, 1995. Thus, inhibitors of the apoptosis suppression or cell survival promoting activity of SRK can be useful to treat autoimmune disease where tolerance has been breached. In general, the present invention relates to methods of regulating a biological response in which SRK, or a homolog thereof, participates, e.g., by being a participant in the biochemical pathway which leads to the ultimate cellular response. For instance, an aspect of the invention relates to methods of modulating signal transduction in which SRK is involved. Since such signal transduction can lead to various biological responses, including transcriptional activation of certain genes. Thus, the invention relates to methods of controlling expression of these genes by modulating SRK activity. Any of the methods described in, e.g., U.S. Pat. Nos. 5,767,075; 5,753,446; 5,728,536; 5,667,314; and 5,459,036 can be utilized in accordance with the present invention, e.g., using SRK, biologically-active fragments thereof, or a homologs thereof. Signal transduction mediated by SRK can be modulated by administering various agents, including antibodies to SRK, a dominant negative SRK gene (see, examples), polypeptide mimics thereof, anti-sense, etc.

The present invention relates to a method of detecting a protein kinase activity in a SRK polypeptide, or a biologically-active polypeptide fragment thereof. Detection of the protein kinase activity of an SRK polypeptide can be accomplished in any suitable way, including in vitro, in vivo, or combinations thereof. For example, kinase assays can be carried at as described in Bagrodia et al., J. Biol. Chem., 270:27995–27998, 1995 or Coso et al., Cell, 81:1137–1146, 1995. Typically, a method of detecting kinase activity in a SRK polypeptide comprises, reacting a human SRK polypeptide, or a biologically-active polypeptide fragment thereof, and a substrate under conditions effective said SRK polypeptide to phosphorylate said substrate; and detecting said phosphorylation of said substrate. Effective conditions, include, e.g., appropriate substrates, $^{32}$P-ATP, pH, buffers, co-factors, etc. For SRK kinase assays, substrates can be, e.g., MBP which is directly phosphorylated by SRK; SRK or a fragment of it; MAPKKs, such as MEK; BAD. Detection can be accomplished in various ways, including gel chromatography, liquid chromatography, in combination with autobiography, e.g., when using radioactive ATP. As discussed above, kinase activity means, e.g., the ability of SRK to transfer a phosphate group from a phosphate donor (e.g., ATP) to a phosphate acceptor (e.g., MBP).

The present invention also relates to methods of identifying substrates for SRK kinase activity. SRK can be contacted with a test substrate, either in vivo or in vitro, under conditions effective for phosphorylation to occur. After a suitable time, the substrate can be isolated and probed for the presence of a phosphate residue. As mentioned, a preferable method of detecting phosphorylation is to use radioactive ATP. However, any suitable detection scheme can be utilized. See, examples below for further guidance.

The present invention also relates to method of identifying agents which modulate a MAPKK stimulatory activity of a human SRK polypeptide, or a biologically-active polypeptide fragment thereof, comprising, administering a test agent to a cell expressing (1) a human SRK polypeptide, or a biologically-active polypeptide fragment thereof, and (2) an MAPKK polypeptide, under conditions effective for said SRK polypeptide to stimulate protein kinase activity of said MAPKK polypeptide; detecting said protein kinase activity; and identifying whether the test agent modulates said stimulatory activity of said SRK polypeptide by comparing the amount of kinase activity in the presence and absence of the test agent. As explained already, MAPKK stimulatory means, e.g., the ability of SRK to activate the kinase activity of MAPKK, itself. Such stimulation can be direct or indirect, e.g., where SRK stimulates a factor which, in turn, stimulates MAPKK. The stimulatory effect is relatively specific for the MAP kinase cascade; JNK1 is poorly stimulated by SRK.

Generally, the term "effective conditions" means, e.g., a milieu in which the desired effect is achieved. Such a milieu, includes, e.g., buffers, oxidizing agents, reducing agents, pH, co-factors, temperature, ion concentrations, suitable age and/or stage of cell (such as, in particular part of the cell cycle, or at a particular developmental stage where particular genes are being expressed) where cells are being used, culture conditions (including substrate, oxygen, carbon dioxide, etc.).

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

The term "administering" as used herein, means, e.g., any suitable delivery technique which is adequate to place the agent in a location where it can elicit an effect. For example, administering can mean contacting a cell or host in an effective manner with the agent of interest, whereby the agent can modulate the activity of interest. Thus, the agent can be administered: in liposomes, as a nucleic acid, in combination with a polymer, in encapsulating agents, in a suitable carrier, etc.

SRK polypeptides can stimulate various MAPKK kinases, including MEK and Ste7. Other MAPKK kinases can be stimulated by SRK can be identified routinely, e.g., as described in the examples.

In the above-mentioned method, SRK and MAPKK polypeptides are expressed in a cell. By the term "expressed" as used herein, it is meant that the cell produces the polypeptides in amounts adequate where SRK's stimulatory activity on MAPKK can be modulated. Any suitable cell line can be used, including cell lines which normally produce the proteins, cell lines which have been induced to produce the proteins, cells lines which have been genetically-engineered to produce SRK and/or MAPKK, etc. In a preferred embodiment, an SRK polypeptide and a MAPKK polypeptide are coded for by nucleic acids which are introduced into a cell line. The nucleic acids can comprise expression control sequences, including promoters (e.g., inducible and constitutive promoters), enhancers, polyadenylation signals, splice sequences, and other elements which are necessary to achieve expression, or which enhance expression. Various cell lines can be suitable as a host, including COS cells (for transient expression), human 293 cells, yeast cells, etc. See, also, above, for other expression methods.

Detecting protein kinase activity can be accomplished routinely. In a preferred embodiment, the aforementioned method of the present invention further includes, steps such as, lysing said cells comprising said expressed SRK polypeptide and MAPKK polypeptides; isolating said MAPKK, and detecting kinase activity in said isolated MAPKK. In this method, the lysing, or breaking apart of the cells, can be performed after the SRK polypeptide had the opportunity to stimulate the MAPKK polypeptide. Lysing can be accomplished conventionally, e.g., by detergent, sonication, homogenization, etc. Whether the test agent modulated the stimulatory activity, can be determined by isolating the MAPKK and testing it for kinase activity. The MAPKK can be isolated in any conventional manner, e.g., chromotography, antibodies, binding ligands, etc. Antibodies can be prepared against MAPKK, itself, or the expressed MAPKK to which an epitope, preferably a polypeptide epitope, has been attached; the cognate antibody can then be used to capture the MAPKK. A more preferred embodiment comprises: contacting said lysate with an anti-epitope antibody, under conditions effective for said antibody to binds to said epitope to form a complex; and then assaying the complex for kinase activity. The nucleic acid can comprise a coding sequence for the MAPKK peptide fused in-frame to a coding sequence for any suitable epitope, including, e.g., KT3, Glu, myc, or a hemaglutinin. Such epitopes are well-known in the art. The antibodies can be attached to any desired substrate, including solid supports, e.g., 96-well plates, nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc In this and other methods described herein, activity can be measured in the presence and absence of a test agent. The objective is to establish a baseline activity, e.g., as in a control, to determine whether the test agent has an effect. Control or baseline values can be obtained simultaneously with, before, after, sequentially, etc., an agent is tested for its effect. By the term "comparing," it is meant, e.g., determining whether the agent affects the desired activity. Generally, such "comparing" is performed by obtaining a value for the activity when the test agent is present and when the test agent is absent; however, other suitable methods can be employed. To determine whether the test agent effects an activity (e.g., apoptosis, kinase, MAPKK stimulatory activity), generally a cell phenotype (e.g., apoptosis; transformation) or activity can be observed in the presence or absence of the agent. This observation does not have to be performed at the same, sequentially, or even on the same day. For instance, once test conditions are established in which the activity or phenotype occurs, it may be unnecessary to repeat the conditions again in the absence of the compound. This is true for all the methods mentioned above and below.

The present invention also relates to methods relating to the role of SRK polypeptides in regulating cellular transformation. As discussed, cellular transformation occurs, e.g., when normally quiescent cells become stimulated to proliferate. Cellular transformation can be measured by any suitable method, including, foci formation (see, examples, where number and/or size of cell foci on plastic or other substrates are examined), growth in soft agar, proportion of cells in the S-phase of the cell cycle, etc. Such methods are known in the art.

In a preferred embodiment of the invention, a method of identifying agents which modulate cellular transformation mediated by Ras and SRK can be accomplished by utilizing a cell line susceptible to transformation in combination with a SRK polypeptide lacking kinase activity (e.g., SRK-KA, SRK-KKAA, SRK-DA, and other dominant negative-acting SRK polypeptides). In a preferred embodiment, a cell line is used which becomes transformed when an activated Ras gene (such as RasV12, e.g., Schafer et al., *Mol. Cell. Bio.*, 5(12):3617–3620, 1985; or RasL61) is introduced into it, e.g., using a nucleic acid containing its coding sequence operably linked to a suitable promoter. See, above, for expression elements and methods. Transformation can be measured as discussed above. Suitable cell lines include, e.g., NIH3 T3, COS, BHK, CHO, human 293, etc. Expression of the SRK polypeptide lacking kinase activity as a nucleic acid, also under the control of a suitable promoter, etc., is also introduced into the cell. Its expression in such cells suppresses the activated Ras foci-forming activity, e.g., reduces, inhibits, interferes with, the activated Ras transforming activity as measured by foci formation. The method can also be performed by assaying for transformation by identifying the ability of the cells to grow in soft agar. The method as described above can identify various types of agents, including those which modify the SRK directly, e.g., impart kinase activity to the kinase-lacking mutein, e.g., by causing a conformation change. Agents can also complement the SRK deficiency by acting as an SRK mimic, acting on a downstream substrate of SRK (e.g., stimulating an MAPKK) in the Ras pathway, causing transcription of an endogenous SRK gene or an SRK replacement, etc.

In related method of identifying agents which modulate cellular transformation mediated by Ras and SRK, a cell line expressing activated Ras is used; however, a SRK lacking kinase activity is not utilized. This method comprises administering a test agent to a cell expressing an activated Ras, e.g., RasV12 polypeptide, under conditions effective for the activated Ras to cause transformation, e.g., as detected in foci-formation assay or soft agar growth assay; identifying whether the test agent modulates the activated Ras transforming activity by comparing the number of transformed cells in the presence or absence of said test compound; and determining whether said test compound modulates an activity of human SRK polypeptide, or a biologically-active polypeptide fragment thereof. Thus in this embodiment of the present invention, once an agent which interferes with Ras transformation is identified, the agent is then tested on SRK to determine whether it modulates an activity of SRK, e.g., a protein kinase activity; an autophosphorylating activity; a cell transforming activity; a cell growth-regulatory activity; a HAX-1 binding activity; an apoptosis suppression activity; a MAPKK activation activity; a transcription modulatory activity, etc. Such activities can be measured as discussed above.

The present invention also relates to the survival regulating activity of SRK, e.g., in preventing apoptosis. The prevention of apoptosis can be useful in treating autoimmune diseases, etc. The invention also relates to methods of identifying agents which modulate the survival regulating activity of a SRK, such as its activity in suppressing apoptosis. This activity can be measured in any suitable way.

As established in the examples, soluble HAX-1 produces apoptosis in cells, e.g., when expressed in mammalian cells, such as COS cells. Expression of SRK reverses this effect. Thus, in one embodiment of the invention, the method comprises: administering a test agent to a cell expressing a soluble HAX-1 polypeptide and a human SRK polypeptide, or a biologically-active polypeptide fragment thereof, wherein said soluble HAX-1polypeptide causes apoptosis in said cell; detecting apoptosis in said cell in the presence and absence of said test compound. Although HAX-1 clone 104 is used in the examples, any other fragment, can be utilized as long as it causes apoptosis. Other useful HAX-1 fragments can be determined routinely, e.g., by following the example below where a HAX-1 nucleic acid is expressed in a cell and DAPI of FACS sorting is used to detect apoptosis. Soluble HAX-1, HAX-1 polypeptides (or other apoptotic-inducing agents, including, genes and proteins), SRK, and SRK fragments, can be administered to a cell in any suitable manner as long as the HAX-1 is effective in causing apoptosis. Any of the mentioned means for delivery can be used, including transfection (calcium phosphate, electroporation, liposome, DEAE, etc.) or other means of introducing a nucleic acid coding for the desired polypeptide or equivalents; introducing the polypeptide directly into the cell (e.g., by conjugating it to a ligand which the cell binds and internalizes, by pinocytosis, etc.). The HAX-1 and SRK can be administered to the cell at the same time, or, sequentially. For example, cells can be co-transfected with the coding sequences. The nucleic acid sequences, as discussed above and below, can be operably linked to expression control sequences. Expression can be induced by using a suitable promoter, or it can be constitutive. These and other appropriate conditions can be determined routinely, e.g., by following the example below to determine effective conditions to induce apoptosis and effective conditions in which apoptosis is suppressed by SRK. An agent can then be administered in any suitable manner to the cell expressing HAX-1 and SRK. Observations can be made at any time, including continuous observations, or observations at predetermined intervals. Apoptosis can be detected according to any known method, including by visual inspection, by staining with DAPI or other chromosomal stains and looking for DNA fragmentation, by propidium iodide stain and FACs (see, e.g., Mohr et al., *Proc. Natl. Acad. Sci.*, 95:5045–5050, 1988; examples below). As with the other methods, agents can be identified which modulate SRK activity by suppressing it, enhancing it, etc.

Thus, another aspect of the invention relates to cytosolic form of a HAX-1 polypeptide, preferably a mammalian HAX-1, more preferably a human HAX-1. See, Suzuki et al., *J. Immunol.*, 158(6): 2737–2744, 1997, for a membrane-bound human HAX-1. As shown in Example 7 below, a cytosolic form of Hax-1 can cause apoptosis when expressed in a mammalian cell line such as COS cells. Such action in causing programmed cell death, i.e., an apoptotic activity, can be useful in variety of ways, including, e.g., to treat tumors (e.g., by causing cell death), to treat autoimmune disease, in assays to identify agents which modulate apoptosis (e.g., see, Example 7), etc. By the term "cytosolic," it is meant that the polypeptide is not membrane-bound or membrane-associated, but is present in the cytoplasm of the cell.

An example of a cytosolic HAX-1 is used in Example 7. This particular cytosolic form of HAX-1 contains amino acids 104–279 of HAX-1 as set forth in FIG. 7. Other cytosolic HAX-1 forms can be determinedly routinely, e.g., by preparing sets of nested deletions, transfecting the clones into cell lines, and localizing the polypeptide produced from by the clone. Localization can be accomplished routinely, e.g., using an epitope tag as described in the examples, using an antibody to a selected portion of HAX-1, using a molecule which binds to HAX-1 and which comprises a detectable label. Other soluble forms of HAX-1 include, about amino acids 104–279 of HAX-1, i.e., where 1, 2, 5, 10, amino acids from HAX-1 or another polypeptide are included at its N- or C-terminus. A cytosolic HAX-1 can be expressed in a variety of cell lines as described above and below, analogously to SRK (e.g., in operative linkage with expression control, etc.). A human cytosolic HAX-1 comprising amino acids 104–279 does not include the full-length sequence shown in FIG. 7 since such full-length sequence is not soluble but is membrane-bound. A human cytosolic HAX-1 can consist essentially of amino acids 104–107 and further comprise a polypeptide epitope (such as the S-peptide, myc, etc.). Such a polypeptide epitope does not affect the activity of cytosolic HAX-1 but permits it to be localized in a cell, immunoprecipitated, etc., utilizing antibodies to the polypeptide epitope.

The above-mentioned method can also be performed by administering a test agent to a cell line under conditions under which apoptosis occurs. In the examples below, SRK is administered to a cell line dependent upon a cytokinin for survival, e.g., FL5.12 cells which require IL-3. Withdrawal of IL-3 for about 18 hours results in apoptosis. Such a protocol is an example of conditions under which apoptosis occurs. Other cell lines can be utilized, e.g., Jurkat cells using the conditions set forth in Zhou et al., Proc. Natl. Acad. Sci., 95:6785–6790, 1998; macrophages using nitric oxide conditions described in Mohr et al., Proc. Natl. Acad. Sci., 95: 5045–5050, 1998; various hemopoietic cells and their cognate CSF's which promote survival (e.g., granulocyte/macrophage cells and GM-CSF, G-CSF, and M-CSF). See, e.g., Alberts et al., Molecular Biology of the Cell, $3^{rd}$ Edition, 1994, page 1169–1175. When SRK is administered to these cells, apoptosis can be suppressed. As with the other methods, agents which modulate this activity can be identified. Inhibition of SRK can be especially useful where apoptosis is desired, e.g., in autoimmune disease.

Another way in which SRK function can be modulated is by regulating a pathway involved in its expression, e.g., modulating its transcription (inducing it), mRNA stability, translation, post-translational modifications, processing (such as cleavage at the internal cleavage site), etc. Expression can be regulated using different agents, e.g., an antisense nucleic acid, a ribozyme, an aptamer, a synthetic compound, or a naturally-occurring compound. Thus, the present invention also relates to a method of identifying agents which induce expression of SRK in cells. Such agents can be identified in the manner described above, i.e., using cells destined (normal program or as a result of artificial conditions) for apoposis, but without the introduction of SRK. Thus, cells can be cultured under conditions under which apoptosis occurs, but without the introduction of SRK. The method further can comprise: administering an agent which suppresses apoptosis; and detecting expression of SRK. Expression can be detected by using an SRK antibody, a nucleic probe for SRK, etc.

The present invention also relates to methods of identifying genes whose transcription is modulated by SRK. For example, activated SRK can be introduced into cells and their expression/transcription patterns can be analyzed in the presence and absence of SRK. Expression analysis can be performed conventionally. For example, high-density oligonucleotide chip arrays can be designed to monitor expression. Such chips can contain all or subsets of the human genome. See, e.g., Anderson et al., Topics in Current Chemistry, 194:117–129, 1998. Southern, Current Biology, 7:85–88, 1996; Marshall and Hodgson, Nature Biotechnology, 16:27–31, 1998.

The present invention also relates to a method of identifying natural ligands and signals which modulate SRK. For instance, cells expressing SRK can be contacted with various cellular products and then assayed for activation of the signal pathway in which SRK is involved. In one embodiment, heterologous SRK is expressed in a cell; such cell is contacted with cells, or products thereof, which have been transformed with a cDNA library. SRK activation is measured routinely as described herein (e.g., by kinase activity, etc). If a transformed cell, or product thereof, results in SRK activation, the cDNA expressed in such transformed cell is then isolated and identified.

Compounds identified in any of the aforementioned assays can be useful to modulate SRK activity in a cell, a tissue, a whole organism, in situ, in vitro (test tube, a solid support, etc.), in vivo, or in any desired environment. In general, a compound having such an in vitro activity will be useful in vivo to modulate a biological pathway associated with SRK, e.g., cell cycle disorders, autoimmune disease, apoptosis, mitogenesis, differentiation, yeast infections (e.g., when modulating a yeast SRK homolog), fertility diseases, heart disease, cancer, metastasis, tumorogenesis, autoimmune disease, blood diseases, etc. Such agents can be agonists or SRK mimics, or antagonists, depending upon the desired effect.

To treat a disease, the compound, or mixture, can be formulated into a pharmaceutical composition comprising a pharmaceutically acceptable carrier and other excipients as apparent to the skilled worker. See, e.g., Remington's Pharmaceutical Sciences, Eighteenth Edition, Mack Publishing Company, 1990. Such composition can additionally contain effective amounts of other compounds.

The present invention also relates to antibodies which specifically recognize SRK. An antibody specific for SRK means that the antibody recognizes a defined sequence of amino acids within or including a SRK, e.g., the human sequence of FIG. 2. Thus, a specific antibody will generally bind with higher affinity to an amino acid sequence, i.e., an epitope, found in FIG. 2 than to a different epitope(s), e.g., as detected and/or measured by an immunoblot assay or other conventional immunoassay. Thus, an antibody which is specific for an epitope of human SRK is useful to detect the presence of the epitope in a sample, e.g., a sample of tissue containing human SRK gene product, distinguishing it from samples in which the epitope is absent. Such antibodies are useful as described in Santa Cruz Biotechnology, Inc., Research Product Catalog, and can be formulated accordingly, e.g., 100 mg/ml. Antibodies, e.g., polyclonal, monoclonal, recombinant, chimeric, humanized, can be prepared according to any desired method. See, also, screening recombinant immunoglobulin libraries (Orlandi et al., Proc. Natl. Acad. Sci., 86:3833–3837, 1989; Huse et al., Science, 256:1275–1281, 1989); in vitro stimulation of lymphocyte populations; Winter and Milstein, Nature, 349: 293–299, 1991. For example, for the production of monoclonal antibodies, a polypeptide according to FIG. 2 can be administered to mice, goats, or rabbit subcutaneously and/or intraperitoneally, with or without adjuvant, in an amount effective to elicit an immune response. The antibodies can also be single chain or FAb fragments. The antibodies can be IgG, subtypes, IgG2a, IgG1, etc. Antibodies, and immune responses, can also be generated by administering naked DNA See, e.g., U.S. Pat. Nos. 5,703,055; 5,589,466; 5,580,859.

SRK, or fragments thereof, for use in the induction of antibodies do not need to have biological activity; however, they must have immunogenic activity, either alone or in combination with a carrier. Peptides for use in the induction of SRK-specific antibodies may have an amino sequence consisting of at least five amino acids, preferably at least 10 amino acids. Short stretches of SRK amino acids, e.g., five amino acids, can be fused with those of another protein such as keyhole limpet hemocyanin, or another useful carrier, and the chimeric molecule used for antibody production.

Several different approaches, as mentioned, can be utilized to prepare antibodies specific for SRK. For instance, in one approach, denatured SRK from purified SRK (e.g., purified by reverse-phase HPLC separation) is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In another approach, an amino acid sequence of SRK, as deduced from the cDNA, is analyzed to determine regions of high immunogenicity. Polypeptides comprising these regions are synthesized and used in suitable immunization protocols to raise antibodies. Analysis to select appropriate epitopes is described by Ausubel FM et al (1989, *Current Protocols in Molecular Biology*, Vol 2. John Wiley & Sons). The optimal amino acid sequences for immunization are usually at the C-terminus, the N-terminus and those intervening, hydrophilic regions of the polypeptide which are likely to be exposed to the external environment when the protein is in its natural conformation. Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas can also be prepared and screened using standard techniques. Hybridomas of interest are detected by screening with labeled SRK to identify those fusions producing the monoclonal antibody with the desired specificity. In a typical protocol, wells of plates (FAST, Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled SRK, 1 mg/ml. Clones producing antibodies will bind a quantity of labeled SRK which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ M, preferably $10^9$ to $10^{10}$, or stronger, will typically be made by standard procedures as described in Harlow and Lane (1988) *Antibodies: A Laboratory Manual*. Cold Spring Harbor Laboratory, or Goding (1986) *Monoclonal Antibodies*: Principles and Practice, $2^{nd}$ Ed. Academic Press N.Y.

Useful sequences for generating antibodies, include, AKQNSSKTTSKRRG. Especially useful sequences include those indicated after the arrow in FIG. 2. Antibodies to such sequences can be useful for distinguishing between the different transcripts of SRK. See, above.

Particular SRK antibodies are useful for the diagnosis of prepathologic conditions, and chronic or acute diseases which are characterized by differences in the amount or distribution of SRK. Diagnostic tests for SRK include methods utilizing the antibody and a label to detect SRK in human (or mouse, etc, if using mouse, etc.) body fluids, tissues or extracts of such tissues.

The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound SRK, using either polyclonal or monoclonal antibodies specific for SRK are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on EC is preferred, but a competitive binding assay may be employed. These assays are described, among other places, in Maddox, Del. et al (1983) *J Exp Med* 158: 1211.

Antibodies and other ligands which bind SRK can be used in various ways, including as therapeutic, diagnostic, and commercial research tools, e.g., to quantitate the levels of SRK polypeptide in animals, tissues, cells, etc., to identify the cellular localization and/or distribution of it, to purify it, or a polypeptide comprising a part of it, to modulate the function of it, in Western blots, ELIZA, immunoprecipitation, RIA, etc. The present invention relates to such assays, compositions and kits for performing them, etc. Utilizing these and other methods, an antibody according to the present invention can be used to detect SRK polypeptide or fragments thereof in various samples, including tissue, cells, body fluid, blood, urine, cerebrospinal fluid. A method of the present invention comprises: a) contacting a ligand which binds to a peptide of FIG. 2 under conditions effective, as known in the art, to achieve binding, and b) detecting specific binding between the ligand and peptide. By specific binding, it is meant that the ligand attaches to a defined sequence of amino acids, e.g., within or including the amino acid sequence of FIG. 2 or derivatives thereof.

Native or recombinant SRK can be purified by immunoaffinity chromatography using SRK-specific antibodies. In general, an immunoaffinity column is constructed by covalently coupling the anti-SRK antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified Ig is covalently attached to a chromatographic resin such as CnBr activated Sepharose (Pharmacia LKB Biotechnology, Piscataway, N.J.). The antibody is coupled to the resin, the resin is blocked, and the derivative resin is washed according to the manufacturer's instructions.

An immunoaffinity column is utilized in the purification of SRK by preparing a fraction from cells containing SRK. This preparation can be derived by solubilization of the whole cell or of a subcellular fraction obtained via differential centrifugation by the addition of detergent or by other methods well known in the art. Alternatively, soluble SRK containing a signal sequence may be secreted in useful quantity into the medium in which the cells are grown.

A soluble SRK-containing preparation is passed over the immunoaffinity column, and the column is washed under conditions, e.g., high ionic strength buffers in the presence of detergent, that allow the preferential absorbance of SRK. Then, the column is eluted under conditions that disrupt antibody/SRK binding (e.g., a buffer of pH 2–3 or a high concentration of a chaotrope such as urea or thiocyanate ion), and the SRK is collected.

In addition, ligands which bind to a SRK polypeptide according to the present invention, or a derivative thereof, can also be prepared, e.g., using synthetic peptide libraries or aptamers (e.g., Pitrung et al., U.S. Pat. No. 5,143,854; Geysen et al., *J. Immunol. Methods*, 102:259–274, 1987; Scott et al., *Science*, 249:386, 1990; Blackwell et al., *Science*, 250:1104, 1990; Tuerk et al., 1990, *Science*, 249: 505.).

The antibodies or derivatives thereof can also be used to inhibit expression of SRK or a fragment thereof. The levels of SRK polypeptide can be determined alone or in combination with other gene products. In particular, the amount (e.g., its expression level) of SRK polypeptide can be compared (e.g., as a ratio) to the amounts of other polypeptides in the same or different sample, e.g., actin. In general, reagents which are specific for SRK can be used in diagnostic and/or forensic studies according to any desired method, e.g., as U.S. Pat. Nos. 5,397,712; 5,434,050; 5,429, 947.

The present invention also relates to a SRK polypeptide, prepared according to a desired method, e.g., as disclosed in U.S. Pat. No. 5,434,050. A labeled polypeptide can be used, e.g., in binding assays, such as to identify substances that bind or attach to SRK, to track the movement of SRK in a cell, in an in vitro, in vivo, or in situ system, etc.

A nucleic acid, polypeptide, antibody, SRK, ligand etc., according to the present invention can be isolated. The term "isolated" means that the material is in a form in which it is not found in its original environment or in nature, e.g., more concentrated, more purified, separated from component, etc. An isolated nucleic acid includes, e.g., a nucleic acid having the sequence of SRK separated from the chromosomal DNA found in a living animal, e.g., as the complete gene, a transcript, or a cDNA. This nucleic acid can be part of a vector or inserted into a chromosome (by specific gene-targeting or by random integration at a position other than its normal position) and still be isolated in that it is not in a form which it is found in its natural environment. A nucleic acid or polypeptide of the present invention can also be substantially purified. By substantially purified, it is meant that nucleic acid or polypeptide is separated and is essentially free from other nucleic acids or polypeptides, i.e., the nucleic acid or polypeptide is the primary and active constituent.

The present invention also relates to a transgenic animal, e.g., a non-human-mammal, such as a mouse, comprising a SRK. Transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology. See, e.g., U.S. Pat. Nos. 4,736,866; 4,873,191; 4,873, 316; 5,082,779; 5,304,489; 5,174,986; 5,175,384; 5,175, 385; 5,221,778; Gordon et al., *Proc. Natl. Acad. Sci.*, 77:7380–7384, 1980; Palmiter et al., *Cell*, 41:343–345, 1985; Palmiter et al., *Ann. Rev. Genet.*, 20:465499, 1986; Askew et al., *Mol. Cell. Bio.*, 13:4115–4124, 1993; Games et al. *Nature*, 373:523–527, 1995; Valancius and Smithies, *Mol. Cell. Bio.*, 11: 1402–1408, 1991; Stacey et al., *Mol. Cell. Bio.*, 14:1009–1016, 1994; Hasty et al., *Nature*, 350:243–246, 1995; Rubinstein et al., *Nucl. Acid Res.*, 21:2613–2617, 1993. A nucleic acid according to the present invention can be introduced into any non-human mammal, including a mouse (Hogan et al., *Manipulating the Mouse Embryo: A Laboratory Manual*, Cold Spring Harbor Laboratory, Cold Spring Harbor, N.Y., 1986), pig (Hammer et al., *Nature*, 315:343–345, 1985), sheep (Hammer et al., *Nature*, 315:343–345, 1985), cattle, rat, or primate. See also, e.g., Church, 1987, *Trends in Biotech*. 5:13–19; Clark et al., *Trends in Biotech*. 5:20–24, 1987); and DePamphilis et al., *BioTechniques*, 6:662–680, 1988). In addition, e.g., custom transgenic rat and mouse production is commercially available. These transgenic animals can useful animals models to test for SRK function, as food for a snake, as a genetic marker to detect strain origin (i.e., where a SRK or fragment thereof has been inserted), etc. Such transgenic animals can further comprise other transgenes. Transgenic animals (such as SRK knockouts) can be prepared and used according to U.S. application Ser. Nos. 08/866,058 and Ser. No. 09/000, 846. A transgenic animal containing a SRK mutant (e.g., a dominant interfering SRK) or a SRK knockout can be combined with other gene mutations, e.g., knockouts or mutations in genes involved in the same or similar signaling pathway. Such genes include: Cdc42 Hs, Racs, Rhos, PAKS, JNK, Jun, WASP, IQGAP, POSH, POR1, p67-phox, MLK3, MAP kinases, NCK, SOS, ERKs, p38, GEFs, GAPs, GDIs, Wiskott-Aldrich Syndrome protein, FTases, STE14, p53, Rb, Mtase, GTPases subunits, Dbl, lbc, Ost, Lsc, Ste7, preferably, Ste11, Fus3, KSS1, Ras, activated Ras muteins, Raf, MEK, etc. and any genes mentioned above, below, or in the references incorporated herein, etc. Animals can be homozygous or heterozygous, depending on the desired use and phenotype.

Generally, the nucleic acids, polypeptides, antibodies, etc. of the present invention can be prepared and used as described in, U.S. Pat. Nos. 5,501,969, 5,506,133, 5,441, 870; WO 90/00607; WO 91/15582.

For other aspects of the nucleic acids, reference is made to standard textbooks of molecular biology. See, e.g., Davis

EXAMPLES

Example 1

Cloning of SRK

To identify novel signal transduction molecules affecting MAP-kinase pathways, we made use of a yeast system in which mammalian Raf and MEK proteins were expressed to complement the yeast Ste11 protein (Freed et al., *Science*, 265:1713–1716, 1994). Strain SY1984, expressing Raf and MEK (SY1984 R-L M-T), responds to Raf activation by signaling through the yeast MAP kinases Kss1 and Fus3. Activation of the latter kinases induces transcription of the HIS3 gene off the FUS1 promoter, which leads to growth in the absence of exogenous histidine (FIG. 1). Cells were transformed with a human cDNA library prepared from Jurkat cells and colonies that grew in the absence of histidine were isolated. cDNAs from each colony were isolated and re-tested in four different strains, the original one used in the screen (SY1984 R-L M-T), a strain that lacked Raf (SY1984 M-T), one that lacked MEK (SY1984 R-L) and a Ste7 null (SY1943-L21), to characterize their functional target.

The screen yielded several genes that activated either Raf, MEK or the yeast MEK, Ste7. Different Ras and 14-3-3 clones were isolated as Raf activators, in that they were capable of stimulating growth in the absence of histidine only when Raf was present. Among the MEK activators, MEKK1 and MEKK2 partial clones encompassing the kinase domains of these genes, were obtained. In addition, two novel genes were isolated as activators of Ste7. They allowed growth on media lacking histidine in the SY1984 strain that has wild type STE7, but not in the strain SY1493-L21, that has a STE7 deletion. These clones, J42 and J207, encoded an identical kinase domain and diverged in the 3' sequences (FIG. 2), suggesting that they might represent splice variants of the same gene. The kinase domain of these genes shares 33% identity with Raf kinase (Bonner et al., *Nucleic Acids Res*, 14:1009–1015, 1986), 37% with Muk (Hirai et al., *Oncogene*, 12:641–650, 1996), 39% with TAKI (Irie et al., *Adv Cancer Res.*, 265:1716–1719, 1994) and 44% with MLK proteins (Dorow et al., *Eur J Biochem*, 213:701–710, 1993), all described as members of the MAP-KKK family. Similarly to the MLK proteins, the J42 kirase domain is followed by a Leucine zipper region that is also present in the J207 clone. The J42 gene has a unique 3' region that encodes a very acidic domain. The isolated J42 cDNA has the potential to encode a protein of 51 KDa calculated MW.

Northern blot analysis using a cDNA probe from the kinase domain identified a predominant band of 7.5 kb and less abundant forms of 3.8 kb and 1.6 kb. A specific probe from the 3' end of J42 identified the large transcript as J42 mRNA, whereas a probe from the 3' end of J207 recognized the 3.8 kb message (FIG. 3A). Analysis of mRNA distribution indicated that J42 and J207 are ubiquitously expressed in normal tissues, but are most abundant in skeletal muscle and heart (FIG. 3B). Because the J42-specific message is the most predominant of the three forms of RNAs, we conducted the following study mainly on the J42 clone. We named the J42 gene "Survival Regulating Kinase," or "SRK."

Other clones can be isolated routinely from cDNA libraries, e.g., libraries which have been prepared by enriching for larger transcripts, e.g, transcripts larger than 5 kb. Since a 7.5 kb SRK transcript is abundant in heart and skeletal muscle, a library can be prepared routinely from mRNA isolated from such tissue. The mRNA can be enriched for longer transcripts by running the mRNA on a gel, cutting out a region of the gel containing the 7.5 kb transcript, and preparing cDNA from the size-enriched mRNA. Once the library is plated out, screening can be performed routinely, e.g., using labeled kinase domain, labeled J42, etc. Screening can also be performed by polymerase chain reaction.

Example 2

Recombinant SRK has Kinase Activity in Vivo and in Vitro

To test whether this novel kinase affected MEK activity in mammalian cells, we co-transfected COS cells with an SRK-KT3 tagged construct and a Glu-tagged MEK plasmid. Subsequently, recombinant MEK was immunoprecipitated with anti-Glu antibodies and subjected to an in vitro kinase reaction in the presence of recombinant ERK. When co-expressed with SRK, the immuno-precipitated MEK was capable of phosphorylating MAP kinase in vitro, indicating that it was activated in vivo. However, when SRK was immunoprecipitated from COS cells and reacted in vitro with recombinant kinase-inactive MEK (MEK-B), it was not capable of phosphorylating and activating MEK, although it was very active against MBP. In contrast, recombinant MEK was quite well phosphorylated and activated by MEKK1. In addition, SRK also displayed strong autophosphorylation. This result suggested that the in vivo activation of MEK by SRK is indirect. Consistent with this hypothesis, SRK caused poor activation of ERK2 when co-expressed in cells. JNK1 was also poorly stimulated by SRK. These observations, together with the sequence homology and the studies in the yeast system, lend support to the hypothesis that SRK may represent a member of a novel MAP kinase pathway.

Example 3

Specific Antibodies Against SRK Identify a 51 KDa Protein as the Major Form of Endogenous SRK in Cells To determine the size of the endogenous SRK protein, we raised rabbit antibodies against a peptide derived from sequences in the carboxy-terminus unique to SRK (FIG. 2). The antiserum was purified on a peptide affinity column and the resulting antibody, 4-1-1, was used in a western blot analysis on lysates from COS and 293 cells. A 250 KDa band that is consistent with the coding potential of the 7.5 Kb SRK transcript. However, a more predominant band of apparent molecular weight of ~51 KDa was consistently observed in cell lysates. This band was detected even when cells were lysed in the presence of high concentration of protease inhibitors or in the presence of SDS. The size of the smaller form is very close to that of the recombinant SRK protein expressed from the cDNA that we identified in the original screen. The slower mobility of the recombinant protein could be caused by the KT3 tag added for identification. Subsequent tests using antibodies raised against recombinant SRK, confirmed that the ~51 kDa endogenous protein has constitutive kinase activity. In addition, limited proteolysis of both the endogenous 51 kDa SRK and the recombinant protein produced similar patterns of peptide fragments.

Example 4

Kinase Defective Mutants of SRK Have Dominant Interfering Properties

Most kinases have a conserved lysine in the active site that is essential for kinase activity. SRK has two consecutive lysines in this region, at position 45 and 46. We mutated one or both of these sites to alanine, as well as the aspartic acid at position 133, that in the context of cdc2 behaves as dominant negative. This generated SRK-K45A (SRK-KA), SRK-K45AK46A (SRK-KKAA) and SRK-D133A (SRK-DA), respectively. To test whether these mutations inactivated the kinase, we expressed the various mutated proteins in yeast as well as in COS cells. None of these mutants were capable of supporting growth on media lacking histidine in the yeast strain SY 1984. Likewise, neither autophosphorylation, nor MBP phosphorylation was observed with these proteins expressed in COS cells (data not shown). To test whether the kinase-inactive SRK mutants behaved as dominant negative mutants, we co-expressed them in yeast with wild type J207, that has the same phenotype in this system, and asked whether the SRK mutants interfered with the ability of J207 to signal to Ste7. Co-expression of these proteins did not affect cell growth in the presence of histidine (+His), indicating the lack of non-specific toxicity to cells. However, when the mutants were expressed on replica plates in the absence of histidine (−His) to test for the activation of the MAP kinase pathway, a lower number of colonies (10–20%) was obtained. No difference in colony numbers on the two media was observed when wild type SRK was expressed. These results indicate that the kinase-inactive SRK mutants bind non-productively to Ste7 and act in a dominant negative fashion in yeast.

Example 5

Figure 4:
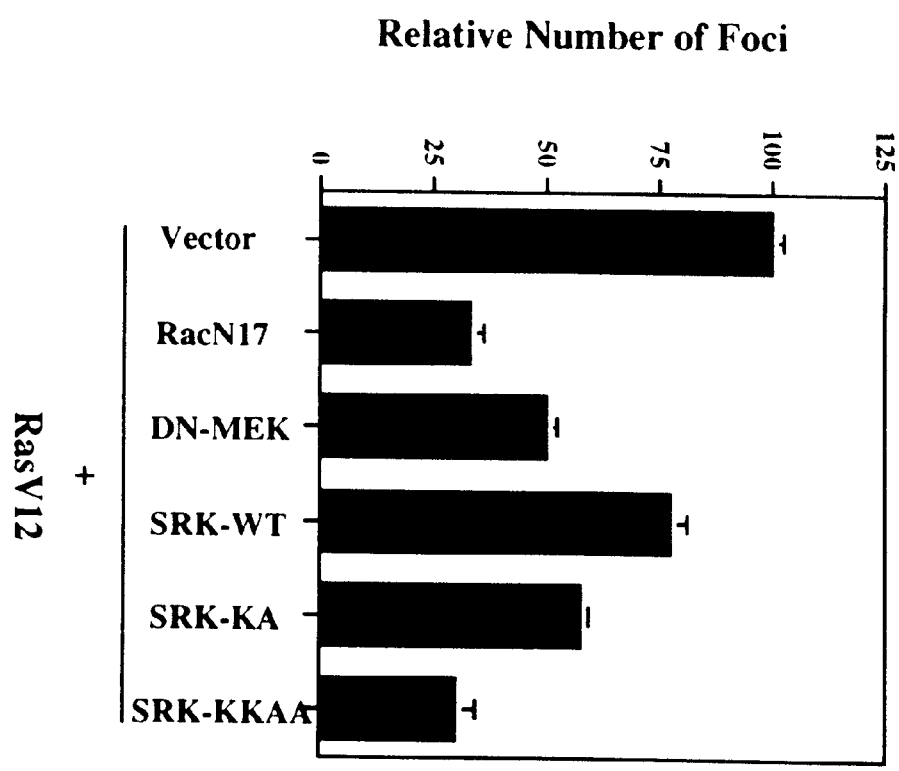
FIG. 4 shows that SRK mutants reduced the ability of Ras to cause foci.

SRK-KA Reduces the Transforming Potential of Ras and Inhibits Growth of 293 Cells in Soft Agar and on Plastic To identify a function for SRK, we asked whether its kinase activity is necessary for oncogenic RasV12 to transform NIH3T3 cells in a focus formation assay. To this end, we co-expressed RasV12 together with the kinase-inactive SRK constructs that might work as dominant interfering mutants in mammalian cells as well as in yeast. FIG. 4 shows that the SRK mutants reduced the ability of Ras to cause foci as did dominant negative MEK and RacN17. To extend this observation to a human cell line, we generated stable lines of human embryonic kidney 293 cells expressing ecdysone-inducible constructs of SRK-KA. Different levels of expression of SRK-KA were observed in different clones after induction with muristerone A. Induction of SRK-KA in these cells affected their growth in a dose-dependent fashion. High expressing clones were more affected in their growth than lower expressing clones, i.e., more growth inhibition was observed in clones expressing larger amounts of SRK-KA than in clones expressing lower amounts. It is interesting to note that some effect on cell growth was observed in some clones even under non-induced conditions. This effect correlated with the background expression levels in the absence of muristerone A in such clones. Interestingly, one clone that showed the tightest expression pattern, was indistinguishable in its growth properties from control cells in the absence of induction. This clone, however, was severely affected after induction of SRK-KA expression. We subsequently tested these clones for their ability to grow in soft agar, a property that is associated with the transformed phenotype. We found that expression of SRK-KA had a dramatic effect on colony formation in soft agar and the degree of the effect also correlated with the expression levels of the mutant SRK protein. Taken together, these observations suggested that SRK has important functions in growth regulation and transformation, as blocking its signaling pathway with the dominant negative mutant interferes with cell transformation.

Example 6

SRK Kinase Binds HAX-1

Figure 5:
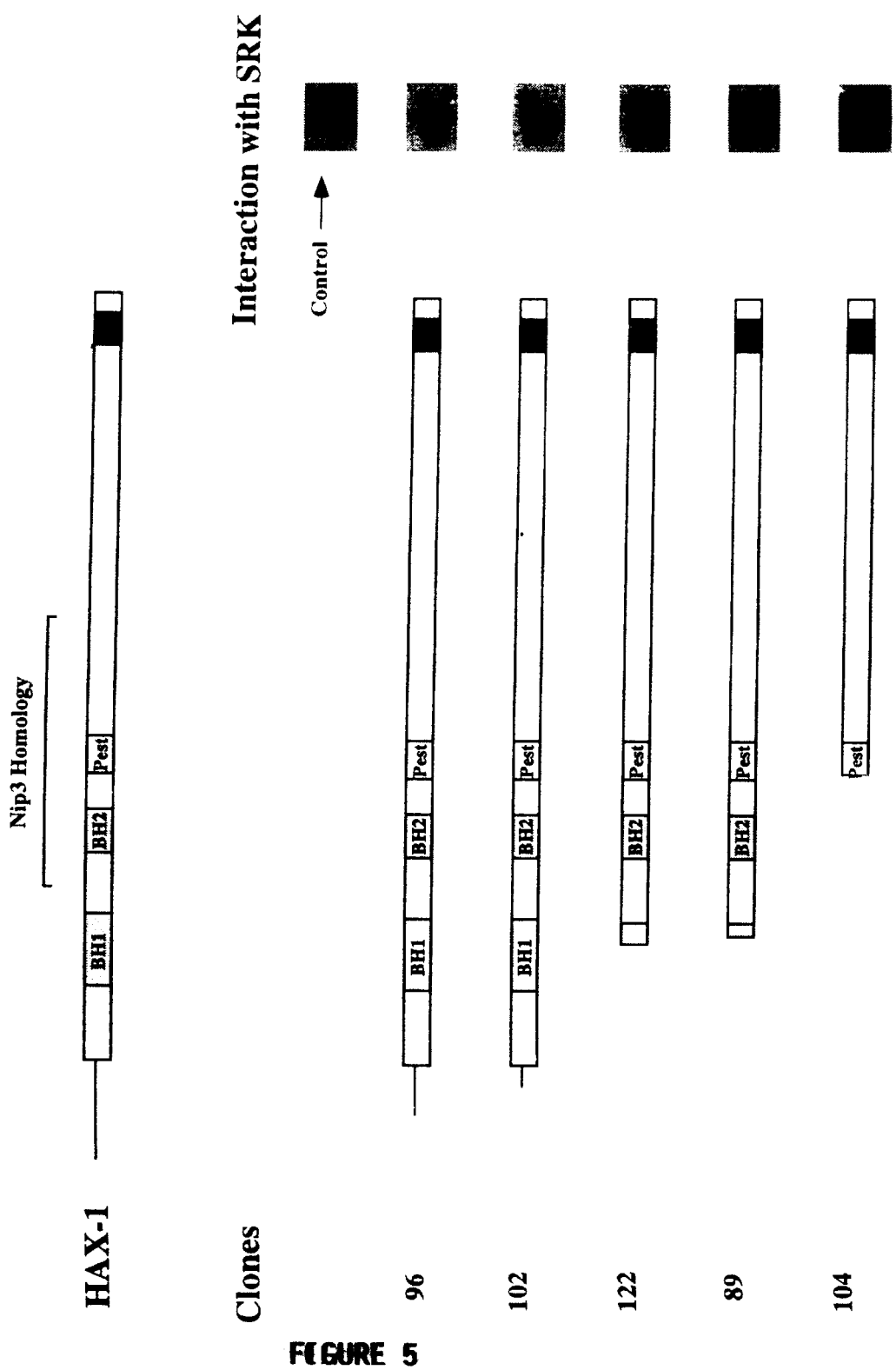
FIG. 5 is a schematic of different fragments of HAX-1.
Figure 6:
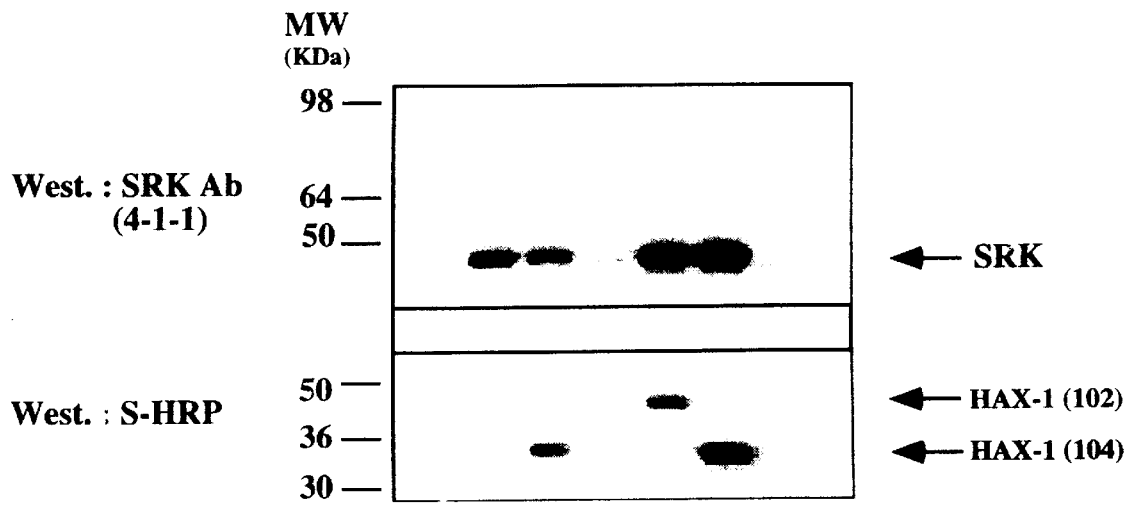
FIG. 6 is data showing that both SRK-WT and SRK-KA are found in HAX-1 complexes.

To delineate a pathway downstream of SRK kinase, we performed a yeast two-hybrid screen with either SRK-WT or SRK-KKAA. In both cases, only the kinase and the Leucine zipper domains were used as bait, because the C-terminal domain of SRK is very acidic and it induced transactivation on its own (data not shown). Strain YRG2 carrying one or the other bait, was transformed with a cDNA library derived from U937 cells. A total of $9.3 \times 10^6$ transformants, $2.6 \times 10^6$ for SRK-WT and $6.7 \times 10^6$ for SRK-KKAA, were a and 318 clones were positive for growth on —His. Since strain YRG2 did not yield a—galactosidase phenotype, the candidates were retested in the YGHI strain for blue color. Similar clones were obtained with SRK-WT and SRK-KKAA. 5 out of 18 total positive clones encoded different fragments of the HAX-1 gene. This genes encodes a protein that shares some homology with proteins of the Bcl-2 family and is localized to mitochondria (Suzuki et al., *J Immunol*, 158:2736–2744, 1997). FIG. 5 shows a schematic of the clones and their -gal phenotype. Interestingly, the strongest interaction was observed with clone 104 lacking the N-terminal half of the protein, indicating that the C-terminal region of Hax-1 is sufficient for binding to SRK. The interaction with SRK was specific, as no interaction was observed with the Gal4 DNA binding domain or with three other baits, Bcl2, p53 or BCR-PH. To confirm interaction in mammalian cells, SRK kinase was co-expressed in COS cells with recombinant S-tagged-Hax-1. FIG. 6 shows that both SRK-WT and SRK-KA are found in S-Hax-1 complexes. The short form of Hax-1, encoded by clone 104, was also found to co-precipitate with both forms of SRK.

Immunofluorescence studies confirmed that full length Hax-1 (clone 102) is predominantly localized to mitochondria, as previously reported (Suzuki et al., *J Immunol*, 158:2736–2744, 1997). Interestingly, a significant fraction of recombinant SRK co-localized to the same organelle. This localization was evident after permeabilization of the cells prior to fixation, which allowed the cytosolic soluble fraction of recombinant SRK to leak out of the cells, revealing the fraction that was anchored via Hax-1 to the mitochondria. In addition to the mitochondrial localization, SRK was also detected in the nucleus.

Example 7

A Soluble Form of Hax-1 Causes Apoptosis

When the C-terminal half of Hax-1 (clone 104, Hax-104) was expressed in COS cells, it did not localize to the mitochondria, despite the presence of the putative hydrophobic transmembrane domain in the C-terminus of the protein. Subcellular fluorescence localization with S-protein, that specifically binds the S-peptide tag on recombinant Hax-1, showed that this truncated protein is cytosolic. Cell permeabilization prior to fixation, lead to total loss of recombinant Hax-104. DAPI staining indicated that Hax-104 expression caused chromosomal condensation typical of cells undergoing apoptosis. This phenotype was not observed with the full length Hax-1 protein, which has been suggested to play a role in suppression of apoptosis (Suzuki et al., *J Immunol*, 158:273&2744, 1997). The toxicity of truncated Hax-1 suggests that this fragment could work as a dominant negative mutant. In an inappropriate location, this partial protein may bind and sequester essential factors, leading to cell death. Interestingly, this effect was suppressed by co-expression with SRK, indicating that SRK may play a role in regulation of apoptosis.

Example 8
SRK-kinase Suppresses Apoptosis in IL-3-dependent Cells

To explore whether SRK may suppress cell death in other systems, we chose to study FL5. 12 cells that have been extensively characterized for their dependence on IL-3 for survival (McCubrey et al., *Oncogene Res.*, 4:97–109, 1989). Cells were transiently transfected with SRK or Bcl2 and allowed to recover for 24 hours. Subsequently, IL-3 was withdrawn for 18 hours and cells were processed for FACS analysis. Expression of SRK reduced the sub-G1 population of cells, that represents cells undergoing DNA fragmentation as a consequence of apoptosis. This reduction was similar to that obtained with Bcl2 in the same experiments. Therefore, also in this system, SRK acts as a suppressor of apoptosis.

Example 9
J42 Phosphorylates BAD In Vitro

The pro-apoptotic (112) protein BAD is (136) inactivated in vivo by phosphorylation at two sites, Ser 112 and Ser 136, which promotes binding of this protein to the 14-3-3 proteins and prevents its interaction with the survival protein Bcl-X. PKB has been shown to be responsible for phosphorylating Ser 136, however, the kinase that phosphorylates Ser 112 in vivo has not been identified yet. As J42 is a serine/threonine kinase and we showed that it is implicated in suppression of apopotosis, we tested whether it would be able to phosphorylate BAD. We first tested BAD phosphorylation in vitro. We incubated recombinant J42 prepared from baculovirus infected cells, with recombinant GAST-BAD and carried out a kinase reaction. J42 was very active on BAD. Phospho-BAD (Ser 112) specific antibodies identified Ser 112 as one of the sites phosphorylated by J42. Interestingly, Serl36 was not affected by J42, but was phosphorylated by PKB.

Example 10
In Vivo Phosphorylation of S112-BAD by J42 In Vivo

To check whether J42 could phosphorylate BAD at S112 in vivo, COS cells were transiently transfected with J42 and with a mutant form of BAD that no longer causes apoptosis ( ). Phosphorylation at site 112 of BAD was then visualized by western blotting of cell lysates using the phospho-112 anti-BAD antibodies. Wt-J42 could increase the levels of phospho-BAD over background levels, whereas J42-KA reduced them. Therefore, J42 is capable of phosphorylating BAD at S112 in vivo.

Example 11
Plasmids and cDNA Library Contructions

The 2 μm-based plasmid pAB23BXN2, containing the URA3 selectable marker, was derived from pAB23-BXN (Schild et al., *Proc Natl Acad Sci USA*, 87:2916–2920, 1990) by inserting a new polylinker (Sal1, Sac 1, Aat II, and Xho 1) between BstX1 and Not1 and used as the library vector. cDNA synthesis was performed on 5 μg of Poly ($A^+$) RNA, isolated from $2 \times 10^8$ Jurkatt cells using the Invitrogen Fast track kit. The first strand was primed with a linker-primer from the ZAP-cDNA synthesis kit (Stratagene) which contains a Xho 1 site. Protection of this 3' cloning site allowed for unidirectional cloning of the finished cDNA. The 5' cloning site was provided by ligation of a BstX1 adaptor. The cDNA library was size fractionated to collect the portion containing inserts above 500 bp and ligated to the prepared vector. Transformation of *E. coli* DH10 beta (GIBCO-BRL) yielded approximatively $1 \times 10^6$ total transformants of which vector religation represented a 3% background.

The human cDNA library from U937 cells, used in the 2-hybrid screen, was a generous gift from Alicia Eguinoa (The Babraham Institute, Cambridge). The library was constructed in the pAD-GAL4 plasmid (Stratagene) between the EcoR1 and the Xho 1 sites. Plasmids pDB-GAL4-SRK-WT C and pDB-GAL4-SRK-KA-C were used as baits. The SRK-kinase inactive mutants were generated using the QuickChange™, Site-Directed Mutagenesis Kit from Stratagene. The following primers were used to convert K45, K46 and D133 to A: GAGGTGGCTGTCGCGAAGCTC-CTCA for SRK-KA, GGTGGCTGTAGCAGCGCTCCT-CAAA for SRK-KKAA, and GTGATTCACAGGGCCCT-CAAGTCAAG for SRK-DA. Mutagenesis was conducted as suggested by the manufacturer. Plasmid EXV and its derivatives containing RacN17, DN-MEK and RasV12 were obtained from Marc Symons (Onyx Pharmaceuticals). pBS-SRK-KT3 was constructed by inserting the KT3 tag after the last codon of SRK, using the following 3' end oligo in a PCR reaction:

GGATCCA
ACACCACCACCAGAACCAGAAACATGA
GCGGCCGC.

The PCDB vector, containing the SV40 promoter, was obtained from George Martin (Onyx Pharmaceuticals) and was used to generate pCDB-SRK-WT, pCDB-SRK-KA and pCDB-SRK-KKAA by subcloning the Sal 1 (filled in)-Not 1 fragments from the pBS constructs. The Hax-1 clones, 102 and 104, represent the full length and N-terminally truncated genes, respectively. They were subcloned from the library plasmids into the pT7Blue-2 vector (Novagen), that provided the S-tag at the N-terminus, and then recloned as Nco 1-filled-in-Hinc II fragments into the filled-in EcoR 1 site of pCDB.

pIND-SRK-KA was contructed using the Hind III -Not 1 fragment of pBS-SRK-KA that contains the KT3-tagged mutant SRK coding sequences, ligated into the p IND (Invitrogen) vector digested with the same enzymes.

Example 12
Yeast Strains and Techniques

Strain SY1984 (MAT ste11 pep4 his3 FUS1::HIS3 leu2 ura3 trp1 can1) (Freed et al., *Science*, 265:1713–1716, 1994) was used to generate its derivatives SY1984 R-L, SY1984 M-T and SY1984 R-L M-T by integration of the RAF (R) and the MEK (M) genes at the LEU2 (L) and the TRP1 (T) loci, respectively. Strain SY1493-L21 (MAT ste11 pep4 his3 FUS1::HIS3 leu2 ura3 trp1 can1 ste7::LEU2) was obtained from Kunihiro Matsumoto (Nagoya University, Japan). Strains YRG2 (Stratagene) and YGH1 (Hannon et al., *Genes Dev*, 7:2378–2391, 1993) were used for the 2-hybrid screen.

Standard yeast media (Rose et al., Cold Spring Harbor Laboratory, Cold Spring Harbor, N.Y., 1988) and genetic techniques (Sherman et al., Cold Spring Laboratory, Cold Spring Harbor, N.Y., 1982) were used.

Example 13
RNA and Protein Analysis

Poly ($A^+$) RNA from HT1080 cells was prepared with the Invitrogen Fast track kit. Human Multiple Tissue Northern Blots I and II were purchased from Clontech and hybridized to the SRK kinase domain probe indicated above. Mammalian cells were lysed in lysis buffer containing 20 mM tris-HCl pH8.0, 137 mM NaCl, 1 mM EGTA, 1% Triton x-100, 10% glycerol, 1.5 mM $MgCl_2$, supplemented prior to use with 1 mM Na orthovanadate, 50 mM NaF, 1 mM Pefabloc, 20 μM Leupeptin and 10 μg/ml Aprotinin. Cells were lysed at 4° C. for 20 minutes and debries were spun at 14 K rpm at 4° C. Typically, 500 μg of proteins were immuno-precipitated with the appropriate antibodies, either coupled to protein G sepharose beads (KT3 antibodies) or together with protein A beads, for 2 hours at 4° C. The immune complexes were washed three times with lysis buffer and the proteins were eluted in Laemmli sample buffer heated for 5 minutes at 95° C. Samples were processed for western blot analysis or for kinase reactions, the latter in the presence of 30 mM Tris-HCl ph 8.0, 20 mM $MgCl_2$, 1 mM EDTA, 75 mM NaCl, 1 mM DTT, 1 mM Na orthovanadate, 10 uM cold ATP, 5 µCurie [-$^{32}$P]ATP and the appropriate substrate.

Immunofluorescence was conducted by fixing cells in 4% formaldehyde for 15 minutes, followed by three washes with PBS, 0.1% Triton x-100 to permeabilize cells and 45 minutes blocking with a blotto solution containing 5% milk powder and 0.1% Tween. When indicated, cell permeabilizion was conducted for 30 seconds prior to fixation.

Antibodies were used at the following dilutions: the SRK 4-1-1 antibodies at 1:200 and the S-FITC protein was diluted 1:2000. Incubation was conducted for 45 minutes. Cells were visualized with an axiovert 100 microscope (Zeiss), using a 40×(0.75 NA) neofluar objective, or a 100×(1.3 NA) plan neofluar objective and pictures were captured with a cooled CCD camera.

Example 14
Cell Transfections

Transient transfection of COS cells was performed using the electroporation protocol as follows. $4 \times 10^6$ cells were trypsinized and washed two times with HeBs buffer, containing 20 mM Hepes pH 7.0, 137 mM NaCl, 5 mM KCl, 0.7 mM Na2 HPO4 and 6 mM Dextrose. Cells were resuspended in a final volume of 260 µl of HeBs, containing 10 µg (1 ug/ml) test DNA and 100 µg of salmon testes carrier DNA. Electroporation was carried out in a Biorad instrument set at 250 volts and 125 µF capacitance. Cells were allowed to recover in the cuvette for 10 minutes, plated in a 10 cm dish and harvested after 72 hours. EcR-293 cells, stably expressing the ecdysone receptor, were purchased from Invitrogen and stably transfected with the SRK-KA or vector plasmids using the SuperFect technique from Qiagen. The selection for transfected cells was carried out in the presence of 300 µg/ml G418 and 400 µg/Zeocin (Invitrogen).

Example 15
Focus Formation Assays, SRB and Soft Agar Growth

Focus formation assays were performed as previously described (Qiu et al. *Nature*, 374:457–459, 1995). Briefly, NIH3T3 cells were transfected with the different DNAs using the calcium phosphate method and foci were counted after 14 days. SRB assays were conducted as described (Skehan et al., *J Natl Cancer Inst*, 82:1107–1112, 1990). Briefly, cells were seeded at $10^4$ cells/well in a 96-well microtiter plate. To achieve reproducibility, seven wells per cell line and two plates for each time point, 0 or 4 days, were tested. After allowing a few hours for attachment, medium was changed and treatments were started. At this point the time 0 plate was fixed to provide for an internal control to use for normalization of data. After four days, cells were fixed with a solution of 50% Trichloroacetic acid. Plates were incubated at 4° C. for 60 minutes, then stained for 30 minutes at room temperature (RT) with 0.2% SRB dissolved in 1% acetic acid and let air dry. The bound dye was solubilized in 200 µl of 10 mM unbuffered Tris base for 5 minutes on a shaker at low speed and the OD was read at 515 nm in an ELISA plate reader.

Soft agar growth was performed as previously described (Qiu et al., *Nature*, 374:457–459, 1995).

Example 16
Apotosis Assays for FL5.12 Cells

FL5.12 cells were cultured to a maximum density of $5 \times 10^5$ cells/ml in RPMI 1640, 10% FCS, 10% WEHI IL-3 supernatant, 2.0 mM L-glutamine, 1.0 mM Sodium Pyruvate, 100 µ/ml penicillin, and 10 µg/ml streptomycin.

DEAE dextran was combined with all transfected DNAs at a ratio of 1.0 µg DEAE dextran/10 pg DNA in a 1.5 ml eppendorf tube at room temperature. FL5.12 cells were harvested by centrifugation and washed twice with cold electroporation medium; RPMI 1640, 20% FCS, 2.0 mM L-glutamine, 1.0 mM Sodium Pyruvate, 100 u/ml penicillin, and 10 µg/ml streptomycin and resuspended at a density of $4 \times 10^7$ cells/ml. 500 µl of the cell suspension was transferred to an eppedorf tube containing the DNA/DEAE dextran complexes. The cell suspensions were incubated on ice for 15 minutes with intermittent mixing (inversion) and transferred into a pre-chilled 0.4 cm Bio-Rad electroporation cuvette. The cells were electroporated in a Bio-Rad Genepulsor electroporator at 250–350V, 960 µF and incubated on ice for 10 minutes. The cells were collected from the cuvette and free genomic DNA was carefully removed with a pipet. The cells were diluted to 5.0 mls with culture medium pre-warmed to 37° C. and carefully overlayered onto 5.0 mls of pre-warmed Ficoll-paque in a 15 mls conical centrifuge tube. Electromoribund cells were separated from surviving cells by centrifugation at 22° C. in a Beckman GS-6R centrifuge equipped with a GS-3.8 rotor and centrifuged at 3000×g for 20 minutes. The cells at the gradient interface were carefully collected and washed 2× with culture medium. The cells were resuspended in 10 mls of culture medium and allowed to recover for 24 hours at 37° C., 5% $CO_2$.

After the 24 hour recovery period the cells were washed 3× with PBS, 1.0% FCS and resuspended in RPMI 1640, 1.0% FCS, 2.0 mM L-glutamine, 1.0 mM sodium pyruvate, 100 u/ml penicillin, 10 µg/ml streptomycin and +/−IL-3. The cells were incubated an additional 18–36 hours under standard environmental conditions.

The cells were washed 2× in cold PBS, 1.0% FCS and resuspended in 500 µl of PBS without calcium or magnesium. The cells were then fixed with 5.0 mls of ice cold 85% ethanol and incubated on ice in the dark for 20 minutes. After fixation, the cells were washed 2× in ice-cold PBS without Ca and Mg and resuspended in 1.0 ml propidium iodide solution: 10 µg/ml propidium iodide, 25 µg/ml Rnase A, 1.0% FCS in PBS without Ca and Mg, and incubated in the dark at 37° C. for 30 minutes. The cells were transferred into a filter cap 4.0 ml polycarbonate tube and analysed by FACS on a Becton-Dickenson FACScalibur scanner.

Discussion

In this study we describe the identification of a novel human serine/threonine kinase, SRK, that in *Saccharomyces cerevisiae* is capable of activating Ste7, the yeast MEK homologue that mediates the mating pheromone response. The SRK protein shares significant homology in the kinase domain to proteins of the MAPKKK family that are known to activate MEKs. The functional identification and the sequence similarities suggest that SRK is a novel member of the MAPKKK family, and may involve another signalling pathway.

Comparison between the length of the isolated SRK cDNA, 2 kb, and that of its mRNA, 7.5 kb, indicates that this is a partial cDNA. We conducted extensive screens of several cDNA libraries to isolate the full length gene, but the longest clones we isolated started at the same point as the originally isolated cDNA. Interestingly, however, the major form of SRK detected in cells has a molecular weight that is very close to that of the protein that is encoded by the isolated cDNA clone.

Mutations in the active site of SRK interfered with its activity in the yeast system. We therefore, used these mutant proteins to investigate roles of SRK in the control of cell proliferation. Focus formation assays indicated that mutated SRK can interfere with Ras-mediated transformation, indicating that its function is needed for oncogenic Ras to exert its full transforming potential. In addition, inducible constructs of dominant negative SRK had a dramatic effect on the ability of 293 cells to grow in soft agar. This phenotype correlated well with the effect on cell growth, as detected with the SRB assay, and was consistent with microscopic observation that showed loss of viability in the culture. Together, these findings indicated a role for SRK in sustaining the transformed phenotype. Some insight into the molecular mechanism by which SRK may regulate transformation was provided by the finding that one of its binding partners is the Hax-1 protein. Hax-1 was identified as an HS1-interacting molecule that shares some homology with the Bcl2 family. The Bcl2 family represents a large group of anti-apoptotic as well as pro-apoptotic factors (Chao et al., *Annu Rev Immunol*, 16:395419, 1998, 1998). These are characterized mainly by shared homology domains that include conserved regions called BH (Bcl Homology) 1, BH2, BH3 and BH4. Hax-1 has the BH1 and BH2 regions, but lacks the BH3 homology (Suzuki et al., *J Immunol*, 158:2736–2744, 1997), the significance of which is unclear. HS1 is a hematopoietic specific protein that transduces signals for both clonal expansion and deletion in lymphoid cells (Taniuchi et al., *EMBO J*, 14:3664–3678, 1995) and it has been implicated in the induction of apoptosis (Fukuda et al., *Proc Natl Acad Sci USA*, 92:7302–7306, 1995). As a binding partner of HS1, Hax-1 was suggested to play a role in mediating cell survival functions (Suzuki et al., *J Immunol*, 158:2736–2744, 1997). We showed that a mutant truncated form of Hax-1, that is no longer membrane localized, caused apoptosis and that SRK could suppress this phenotype. In addition, SRK suppressed cell death induced by removal of IL-3 in FL5.12 cells.

Recently, it has become apparent that oncogenes, in addition to deregulating growth, also induce cell death (Evan et al., *Cell*, 69:119–128, 1992; Shi et al., *Science*, 257:212–214, 1992). Suppression of apoptosis in cells harboring oncogenic mutations is, therefore, a prerequisite for progression into a transformed phenotype. Such suppression can be brought about by loss of pro-apoptotic factors, like Bax (Rampino et al., *Science*, 275:967–969, 1997), or by overproduction of survival factors or their receptors, such as IGF-1 and IGF-1R (Yee et al., *Cancer Treat Res*, 53:93–106, 1991; Cullen et al., *Cancer Invest*, 9:443–454, 1991). Phosphorylation events implicated in suppression of apoptosis have been described for regulation of Bcl-2 (Ito et al., 1997; May et al., 1994) as well as BAD activities (Zha et al., 1996).

The co-localization of Hax-1 and SRK indicate a model in which SRK binding to Hax-1 allows this kinase to be appropriately positioned to phosphorylate pro-apoptotic proteins, such as HS 1 in lymphatic cells, or its counterpart(s) in other cell types. This modification can prevent pro-apoptotic proteins from binding to Hax-1 and reduce their toxic effect. Our findings indicate that inhibition of SRK activity can lead transformed cells to undergo apoptosis, therefore, SRK represents a useful target for therapeutic intervention in cancer.

Without further elaboration, it is believed that one skilled in the art can, using the preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

What is claimed:

1. An isolated nucleic acid comprising a nucleotide sequence, as set forth in SEQ ID No. 1, coding for a full-length SRK, wherein, the biological activities are selected from the group consisting of a protein kinase activity; an autophosphorylating activity; a cell growth regulatory activity; a HAX-1 (HF1-Associated Protein-1) binfing activity; an apoptosis suppression activity; a MAPKK (Mitogen-Activated Protein Kinase Kinase) stimulatory activity; and a SRK-specific immunogenic activity.

2. An isolated nucleic acid of claim 1, wherein said nucleic acid is coded-for by an mRNA which is 7.5 kb, 3.8 kb, or 1.6 kb.

3. An isolated nucleic acid of claim 1, wherein the nucleotide sequence codes for amino acid 1 to amino acid 455 as set forth in (SEQ. ID. No. 2).

4. An isolated nucleic acid of claim 1, wherein the nucleotide sequence is operably linked to an expression control sequence.

5. An isolated nucleic acid of claim 1, wherein the nucleic acid further comprises a detectable label.

6. A method of expressing in transformed host cells, a human SRK₂ (Survival Regulating Kinase), polypeptide, as set forth in SEQ. ID. No. 2, coded for by a nucleic acid, comprising:

culturally transformed host cells containing a nucleic acid of claim 1 under conditions effective to express the polypeptide.

7. A method of claim 6, wherein said host cells are mammalian.

8. A method of claim 6, wherein said host cells are yeast.

9. A method of claim 6, further comprising isolating said human SRK.

10. A transformed host cell containing a nucleic acid of claim 1.

11. A vector comprising a nucleic acid of claim 1.

* * * * *

SEQUENCE LISTING

```
<160> NUMBER OF SEQ ID NOS: 9

<210> SEQ ID NO 1
<211> LENGTH: 2119
<212> TYPE: DNA
<213> ORGANISM: Human J42
<220> FEATURE:
<221> NAME/KEY: CDS
<222> LOCATION: Complement((52)..(1416))

<400> SEQUENCE: 1
gcccgcccgg gagccagatt ttgtggaagt ataatacttt gtcattatga g atg tcg      57
                                                          Met Ser
                                                            1 tct ctc ggt gcc tcc ttt gtg caa att aaa ttt gat gac ttg cag ttt    105
Ser Leu Gly Ala Ser Phe Val Gln Ile Lys Phe Asp Asp Leu Gln Phe
         5                  10                  15 ttt gaa aac tgc ggt gga gga agt ttt ggg agt gtt tat cga gcc aaa    153
Phe Glu Asn Cys Gly Gly Gly Ser Phe Gly Ser Val Tyr Arg Ala Lys
        20                  25                  30 tgg ata tca cag gac aag gag gtg gct gta aag aag ctc ctc aaa ata    201
Trp Ile Ser Gln Asp Lys Glu Val Ala Val Lys Lys Leu Leu Lys Ile
 35                  40                  45                  50 gag aaa gag gca gaa ata ctc agt gtc ctc agt cac aga aac atc atc    249
Glu Lys Glu Ala Glu Ile Leu Ser Val Leu Ser His Arg Asn Ile Ile
```

```
                              55                      60                      65
cag ttt tat gga gta att ctt gaa cct ccc aac tat ggc att gtc aca        297
Gln Phe Tyr Gly Val Ile Leu Glu Pro Pro Asn Tyr Gly Ile Val Thr
                70                      75                      80 gaa tat gct tct ctg gga tca ctc tat gat tac att aac agt aac aga        345
Glu Tyr Ala Ser Leu Gly Ser Leu Tyr Asp Tyr Ile Asn Ser Asn Arg
            85                      90                      95 agt gag gag atg gat atg gat cac att atg acc tgg gcc act gat gta        393
Ser Glu Glu Met Asp Met Asp His Ile Met Thr Trp Ala Thr Asp Val
        100                     105                     110 gcc aaa gga atg cat tat tta cat atg gag gct cct gtc aag gtg att        441
Ala Lys Gly Met His Tyr Leu His Met Glu Ala Pro Val Lys Val Ile
115                     120                     125                     130 cac aga gac ctc aag tca aga aac gtt gtt ata gct gct gat gga gta        489
His Arg Asp Leu Lys Ser Arg Asn Val Val Ile Ala Ala Asp Gly Val
                135                     140                     145 ttg aag atc tgt gac ttt ggt gcc tct cgg ttc cat aac cat aca aca        537
Leu Lys Ile Cys Asp Phe Gly Ala Ser Arg Phe His Asn His Thr Thr
            150                     155                     160 cac atg tcc ttg gtt gga act ttc cca tgg atg gct cca gaa gtt atc        585
His Met Ser Leu Val Gly Thr Phe Pro Trp Met Ala Pro Glu Val Ile
        165                     170                     175 cag agt ctc cct gtg tca gaa act tgt gac aca tat tcc tat ggt gtg        633
Gln Ser Leu Pro Val Ser Glu Thr Cys Asp Thr Tyr Ser Tyr Gly Val
    180                     185                     190 gtt ctc tgg gag atg cta aca agg gag gtc ccc ttt aaa ggt ttg gaa        681
Val Leu Trp Glu Met Leu Thr Arg Glu Val Pro Phe Lys Gly Leu Glu
195                     200                     205                     210 gga tta caa gta gct tgg ctt gta gtg gaa aaa aac gag aga tta acc        729
Gly Leu Gln Val Ala Trp Leu Val Val Glu Lys Asn Glu Arg Leu Thr
                215                     220                     225 att cca agc agt tgc ccc aga agt ttt gct gaa ctg tta cat cag tgt        777
Ile Pro Ser Ser Cys Pro Arg Ser Phe Ala Glu Leu Leu His Gln Cys
            230                     235                     240 tgg gaa gct gat gcc aag aaa cgg cca tca ttc aag caa atc att tca        825
Trp Glu Ala Asp Ala Lys Lys Arg Pro Ser Phe Lys Gln Ile Ile Ser
        245                     250                     255 atc ctg gag tcc atg tca aat gac acg agc ctt cct gac aag tgt aac        873
Ile Leu Glu Ser Met Ser Asn Asp Thr Ser Leu Pro Asp Lys Cys Asn
    260                     265                     270 tca ttc cta cac aac aag gcg gag tgg agg tgc gaa att gag gca act        921
Ser Phe Leu His Asn Lys Ala Glu Trp Arg Cys Glu Ile Glu Ala Thr
275                     280                     285                     290 ctt gag agg cta aag aaa cta gag cgt gat ctc agc ttt aag gag cag        969
Leu Glu Arg Leu Lys Lys Leu Glu Arg Asp Leu Ser Phe Lys Glu Gln
                295                     300                     305 gag ctt aaa gaa cga gaa aga cgt tta aag atg tgg gag caa aag ctg        1017
Glu Leu Lys Glu Arg Glu Arg Arg Leu Lys Met Trp Glu Gln Lys Leu
            310                     315                     320 aca gag cag tcc aac acc ccg ctt ctc ttg cct ctt gct gca aga atg        1065
Thr Glu Gln Ser Asn Thr Pro Leu Leu Leu Pro Leu Ala Ala Arg Met
        325                     330                     335 tct gag gag tct tac ttt gaa tct aaa aca gag gag tca aac agt gca        1113
Ser Glu Glu Ser Tyr Phe Glu Ser Lys Thr Glu Glu Ser Asn Ser Ala
    340                     345                     350 gag atg tca tgt cag atc aca gca aca agt aac ggg gag ggc cat ggc        1161
Glu Met Ser Cys Gln Ile Thr Ala Thr Ser Asn Gly Glu Gly His Gly
355                     360                     365                     370 atg aac cca agt ctg cag gcc atg atg ctg atg ggc ttt ggg gat atc        1209
```

```
Met Asn Pro Ser Leu Gln Ala Met Met Leu Met Gly Phe Gly Asp Ile
            375                 380                 385 ttc tca atg aac aaa gca gga gct gtg atg cat tct ggg atg cag ata      1257
Phe Ser Met Asn Lys Ala Gly Ala Val Met His Ser Gly Met Gln Ile
            390                 395                 400 aac atg caa gcc aag cag aat tct tcc aaa acc aca tct aag aga agg      1305
Asn Met Gln Ala Lys Gln Asn Ser Ser Lys Thr Thr Ser Lys Arg Arg
            405                 410                 415 ggg aag aaa gtc aac atg gct ctg ggg ttc agt gat ttt gac ttg tca      1353
Gly Lys Lys Val Asn Met Ala Leu Gly Phe Ser Asp Phe Asp Leu Ser
            420                 425                 430 gaa ggt gac gat gat gat gat gac ggt gag gag gag gat aat gac          1401
Glu Gly Asp Asp Asp Asp Asp Asp Gly Glu Glu Glu Asp Asn Asp
435                 440                 445                 450 atg gat aat agt gaa tgaaagcaga aagcaaagta ataaaatcac aaatgtttgg      1456
Met Asp Asn Ser Glu
            455 aaaacacaaa agtaacttgt ttatctcagt ctgtacaaaa acagtaagga ggcagaaagc   1516 caagcactgc attttaggc caatcacatt tacatgaccg taatttctta tcaattctac    1576 ttttatttt gcttacagaa aaacggggg agaattaagc caaagaagta tatttatgaa    1636 tcagcaaatg tggtgcctga ttatagaaat ttgtgatccc tatatacaat ataggatttt   1696 taaagttgag acattctggc ttttctttt aatgaatact ttttagtttg tattggactt    1756 tatttccttt attcaaatca ttttaaaaa ctaacatttt gaacaaacat tcttaactcc    1816 taattgttct tagacacgta gtaattctgt gacatacttt ttttttctta tagcaataca   1876 ctgtaatatc agaaatggtt ggcctgagca acctagtaag acttcgtctc tactaataat   1936 taaaaaacta gctggcatgg tagcacacac ctgtagtccc agatacttgg gaggccaagg   1996 caggaggatt gcttgagacc tagcaatcag tcagggctgc agtgagccat gaggcaccac   2056 tgcactctag cctgggcaag agaacaagat cctgtctcaa aaacaaaaa aaaaaaaaa     2116 aaa                                                                 2119

<210> SEQ ID NO 2
<211> LENGTH: 455
<212> TYPE: PRT
<213> ORGANISM: Human J42

<400> SEQUENCE: 2

Met Ser Ser Leu Gly Ala Ser Phe Val Gln Ile Lys Phe Asp Asp Leu
 1               5                  10                  15

Gln Phe Phe Glu Asn Cys Gly Gly Gly Ser Phe Gly Ser Val Tyr Arg
            20                  25                  30

Ala Lys Trp Ile Ser Gln Asp Lys Glu Val Ala Val Lys Lys Leu Leu
        35                  40                  45

Lys Ile Glu Lys Glu Ala Glu Ile Leu Ser Val Leu Ser His Arg Asn
    50                  55                  60

Ile Ile Gln Phe Tyr Gly Val Ile Leu Glu Pro Pro Asn Tyr Gly Ile
65                  70                  75                  80

Val Thr Glu Tyr Ala Ser Leu Gly Ser Leu Tyr Asp Tyr Ile Asn Ser
                85                  90                  95

Asn Arg Ser Glu Glu Met Asp Met Asp His Ile Met Thr Trp Ala Thr
            100                 105                 110

Asp Val Ala Lys Gly Met His Tyr Leu His Met Glu Ala Pro Val Lys
        115                 120                 125
```

```
Val Ile His Arg Asp Leu Lys Ser Arg Asn Val Ile Ala Ala Asp
            130                 135                 140

Gly Val Leu Lys Ile Cys Asp Phe Gly Ala Ser Arg Phe His Asn His
145                 150                 155                 160

Thr Thr His Met Ser Leu Val Gly Thr Phe Pro Trp Met Ala Pro Glu
                165                 170                 175

Val Ile Gln Ser Leu Pro Val Ser Glu Thr Cys Asp Thr Tyr Ser Tyr
                180                 185                 190

Gly Val Val Leu Trp Glu Met Leu Thr Arg Glu Val Pro Phe Lys Gly
            195                 200                 205

Leu Glu Gly Leu Gln Val Ala Trp Leu Val Val Glu Lys Asn Glu Arg
        210                 215                 220

Leu Thr Ile Pro Ser Ser Cys Pro Arg Ser Phe Ala Glu Leu Leu His
225                 230                 235                 240

Gln Cys Trp Glu Ala Asp Ala Lys Lys Arg Pro Ser Phe Lys Gln Ile
                245                 250                 255

Ile Ser Ile Leu Glu Ser Met Ser Asn Asp Thr Ser Leu Pro Asp Lys
                260                 265                 270

Cys Asn Ser Phe Leu His Asn Lys Ala Glu Trp Arg Cys Glu Ile Glu
            275                 280                 285

Ala Thr Leu Glu Arg Leu Lys Lys Leu Glu Arg Asp Leu Ser Phe Lys
        290                 295                 300

Glu Gln Glu Leu Lys Glu Arg Glu Arg Arg Leu Lys Met Trp Glu Gln
305                 310                 315                 320

Lys Leu Thr Glu Gln Ser Asn Thr Pro Leu Leu Pro Leu Ala Ala
                325                 330                 335

Arg Met Ser Glu Glu Ser Tyr Phe Glu Ser Lys Thr Glu Glu Ser Asn
                340                 345                 350

Ser Ala Glu Met Ser Cys Gln Ile Thr Ala Thr Ser Asn Gly Glu Gly
            355                 360                 365

His Gly Met Asn Pro Ser Leu Gln Ala Met Met Leu Met Gly Phe Gly
        370                 375                 380

Asp Ile Phe Ser Met Asn Lys Ala Gly Ala Val Met His Ser Gly Met
385                 390                 395                 400

Gln Ile Asn Met Gln Ala Lys Gln Asn Ser Ser Lys Thr Thr Ser Lys
                405                 410                 415

Arg Arg Gly Lys Lys Val Asn Met Ala Leu Gly Phe Ser Asp Phe Asp
            420                 425                 430

Leu Ser Glu Gly Asp Asp Asp Asp Asp Gly Glu Glu Glu Asp
        435                 440                 445

Asn Asp Met Asp Asn Ser Glu
    450                 455

<210> SEQ ID NO 3
<211> LENGTH: 1196
<212> TYPE: DNA
<213> ORGANISM: Human HAX-1
<220> FEATURE:
<221> NAME/KEY: CDS
<222> LOCATION: Complement((162)..(998))

<400> SEQUENCE: 3
aggtccggct taccgtcgtt tacgacagtg tcaggatcgc gggcttgctt tccggtagcg     60
tgggctgacg cctcgctcaa tttctcacag ggctgcgcag gttgccccg tctgcgaatg    120 gaccactgga ggggttcaaa ggttcgcgtc ccagtacggg a atg agc ctc ttt gat    176
```

-continued

```
                                  Met Ser Leu Phe Asp
                                   1               5
ctc ttc cgg ggc ttt ttc ggc ttt cct gga cct cgg agc cac aga gat    224
Leu Phe Arg Gly Phe Phe Gly Phe Pro Gly Pro Arg Ser His Arg Asp
             10                  15                  20 ccc ttt ttt gga ggg atg act cga gat gaa gat gat gat gag gaa gaa    272
Pro Phe Phe Gly Gly Met Thr Arg Asp Glu Asp Asp Asp Glu Glu Glu
                 25                  30                  35 gaa gaa gaa ggg ggc tca tgg ggc cgt ggg aac cca agg ttc cat agt    320
Glu Glu Glu Gly Gly Ser Trp Gly Arg Gly Asn Pro Arg Phe His Ser
             40                  45                  50 cct cag cac ccc cct gag gaa ttt ggc ttc ggc ttc agc ttc agc cca    368
Pro Gln His Pro Pro Glu Glu Phe Gly Phe Gly Phe Ser Phe Ser Pro
         55                  60                  65 gga gga ggg ata cgt ttc cac gat aac ttc ggc ttt gat gac cta gta    416
Gly Gly Gly Ile Arg Phe His Asp Asn Phe Gly Phe Asp Asp Leu Val
     70                  75                  80                  85 cga gat ttc aat agc atc ttc agc gat atg ggg gcc tgg acc ttg cct    464
Arg Asp Phe Asn Ser Ile Phe Ser Asp Met Gly Ala Trp Thr Leu Pro
                 90                  95                 100 tcc cat cct cct gaa ctt cca ggt cct gag tca gag aca cct ggt gag    512
Ser His Pro Pro Glu Leu Pro Gly Pro Glu Ser Glu Thr Pro Gly Glu
             105                 110                 115 aga cta cgg gag gga cag aca ctt cgg gac tca atg ctt aag tat cca    560
Arg Leu Arg Glu Gly Gln Thr Leu Arg Asp Ser Met Leu Lys Tyr Pro
         120                 125                 130 gat agt cac cag ccc agg atc ttt ggg ggg gtc ttg gag agt gat gca    608
Asp Ser His Gln Pro Arg Ile Phe Gly Gly Val Leu Glu Ser Asp Ala
     135                 140                 145 aga agt gaa tcc ccc caa cca gca cca gac tgg ggc tcc cag agg cca    656
Arg Ser Glu Ser Pro Gln Pro Ala Pro Asp Trp Gly Ser Gln Arg Pro
150                 155                 160                 165 ttt cat agg ttt gat gat gta tgg cct atg gac ccc cat cct aga acc    704
Phe His Arg Phe Asp Asp Val Trp Pro Met Asp Pro His Pro Arg Thr
                 170                 175                 180 aga gag gac aat gat ctt gat tcc cag gtt tcc cag gag ggt ctt ggc    752
Arg Glu Asp Asn Asp Leu Asp Ser Gln Val Ser Gln Glu Gly Leu Gly
             185                 190                 195 ccg gtt cta cag ccc cag ccc aaa tcc tat ttc aag agc atc tct gtg    800
Pro Val Leu Gln Pro Gln Pro Lys Ser Tyr Phe Lys Ser Ile Ser Val
         200                 205                 210 acc aag atc act aaa cca gat ggg ata gtg gag gag cgc cgg act gtg    848
Thr Lys Ile Thr Lys Pro Asp Gly Ile Val Glu Glu Arg Arg Thr Val
     215                 220                 225 gtg gac agt gag ggc cgg aca gag act aca gta acc cga cac gaa gca    896
Val Asp Ser Glu Gly Arg Thr Glu Thr Thr Val Thr Arg His Glu Ala
230                 235                 240                 245 gat agc agt cct agg ggt gat cca gaa tca cca aga cct cca gcc ctg    944
Asp Ser Ser Pro Arg Gly Asp Pro Glu Ser Pro Arg Pro Pro Ala Leu
                 250                 255                 260 gat gat gcc ttt tcc atc ctg gac tta ttc ctg gga cgt tgg ttc cgg    992
Asp Asp Ala Phe Ser Ile Leu Asp Leu Phe Leu Gly Arg Trp Phe Arg
             265                 270                 275 tcc cgg tagccttgtt aaccctcaga ggccttcaag tcctttccac ctctcaccca   1048
Ser Arg ttgcccacca ttaataagct tagcttctct tgccacctca ggggcttgga tatgtggaat   1108
agtgaactgg ggccatgtca gtttgtcact cacccaaact gaccaataaa acctttattt   1168
atgctaaaaa aaaaaaaaaa aaaaaaaa                                      1196
```

```
<210> SEQ ID NO 4
<211> LENGTH: 279
<212> TYPE: PRT
<213> ORGANISM: Human HAX-1

<400> SEQUENCE: 4

Met Ser Leu Phe Asp Leu Phe Arg Gly Phe Phe Gly Phe Pro Gly Pro
 1               5                  10                  15

Arg Ser His Arg Asp Pro Phe Phe Gly Gly Met Thr Arg Asp Glu Asp
                20                  25                  30

Asp Asp Glu Glu Glu Glu Glu Gly Gly Ser Trp Gly Arg Gly Asn
            35                  40                  45

Pro Arg Phe His Ser Pro Gln His Pro Pro Glu Glu Phe Gly Phe Gly
    50                  55                  60

Phe Ser Phe Ser Pro Gly Gly Gly Ile Arg Phe His Asp Asn Phe Gly
 65                  70                  75                  80

Phe Asp Asp Leu Val Arg Asp Phe Asn Ser Ile Phe Ser Asp Met Gly
                85                  90                  95

Ala Trp Thr Leu Pro Ser His Pro Pro Glu Leu Pro Gly Pro Glu Ser
            100                 105                 110

Glu Thr Pro Gly Glu Arg Leu Arg Glu Gly Gln Thr Leu Arg Asp Ser
        115                 120                 125

Met Leu Lys Tyr Pro Asp Ser His Gln Pro Arg Ile Phe Gly Gly Val
130                 135                 140

Leu Glu Ser Asp Ala Arg Ser Glu Ser Pro Gln Pro Ala Pro Asp Trp
145                 150                 155                 160

Gly Ser Gln Arg Pro Phe His Arg Phe Asp Val Trp Pro Met Asp
                165                 170                 175

Pro His Pro Arg Thr Arg Glu Asp Asn Asp Leu Asp Ser Gln Val Ser
            180                 185                 190

Gln Glu Gly Leu Gly Pro Val Leu Gln Pro Gln Pro Lys Ser Tyr Phe
        195                 200                 205

Lys Ser Ile Ser Val Thr Lys Ile Thr Lys Pro Asp Gly Ile Val Glu
    210                 215                 220

Glu Arg Arg Thr Val Val Asp Ser Glu Gly Arg Thr Glu Thr Thr Val
225                 230                 235                 240

Thr Arg His Glu Ala Asp Ser Ser Pro Arg Gly Asp Pro Glu Ser Pro
                245                 250                 255

Arg Pro Pro Ala Leu Asp Asp Ala Phe Ser Ile Leu Asp Leu Phe Leu
            260                 265                 270

Gly Arg Trp Phe Arg Ser Arg
        275

<210> SEQ ID NO 5
<211> LENGTH: 14
<212> TYPE: PRT
<213> ORGANISM: SRK-KA

<400> SEQUENCE: 5

Ala Lys Gln Asn Ser Ser Lys Thr Thr Ser Lys Arg Arg Gly
 1               5                  10

<210> SEQ ID NO 6
<211> LENGTH: 25
<212> TYPE: DNA
<213> ORGANISM: SRK-KKAA
```

-continued

```
<400> SEQUENCE: 6
gaggtggctg tcgcgaagct cctca                                              25

<210> SEQ ID NO 7
<211> LENGTH: 25
<212> TYPE: DNA
<213> ORGANISM: SRK-DA

<400> SEQUENCE: 7
ggtggctgta gcagcgctcc tcaaa                                              25

<210> SEQ ID NO 8
<211> LENGTH: 26
<212> TYPE: DNA
<213> ORGANISM: pBS-SRK-KT3

<400> SEQUENCE: 8
gtgattcaca gggccctcaa gtcaag                                             26

<210> SEQ ID NO 9
<211> LENGTH: 42
<212> TYPE: DNA
<213> ORGANISM: pBS-SRK-KT3

<400> SEQUENCE: 9
ggatccaaca ccaccaccag aaccagaaac atgagcggcc gc                           42
```